(12) United States Patent
Ikishima et al.

(10) Patent No.: US 11,141,326 B2
(45) Date of Patent: Oct. 12, 2021

(54) ULTRASMALL SECURING TAPE AND ARTICLE INCLUDING SAME

(71) Applicant: NITTO DENKO CORPORATION, Osaka (JP)

(72) Inventors: Shinsuke Ikishima, Ibaraki (JP); Muneshige Nakagawa, Ibaraki (JP)

(73) Assignee: NITTO DENKO CORPORATION, Osaka (JP)

( * ) Notice: Subject to any disclaimer, the term of this patent is extended or adjusted under 35 U.S.C. 154(b) by 440 days.

(21) Appl. No.: 15/767,243

(22) PCT Filed: Oct. 14, 2016

(86) PCT No.: PCT/JP2016/080490
§ 371 (c)(1),
(2) Date: Apr. 10, 2018

(87) PCT Pub. No.: WO2017/069050
PCT Pub. Date: Apr. 27, 2017

(65) Prior Publication Data
US 2019/0076308 A1 Mar. 14, 2019

(30) Foreign Application Priority Data
Oct. 22, 2015 (JP) .............................. JP2015-207993

(51) Int. Cl.
| | | |
|---|---|---|
| *A61F 13/58* | (2006.01) | |
| *B32B 27/00* | (2006.01) | |
| *C09J 201/00* | (2006.01) | |
| *C09J 7/20* | (2018.01) | |
| *B32B 7/04* | (2019.01) | |
| *B32B 7/05* | (2019.01) | |
| *A61F 13/62* | (2006.01) | |
| *C09J 7/24* | (2018.01) | |
| *B32B 5/02* | (2006.01) | |
| *B32B 27/12* | (2006.01) | |
| *B32B 27/20* | (2006.01) | |
| *B32B 27/30* | (2006.01) | |
| *B32B 27/32* | (2006.01) | |
| *B32B 27/36* | (2006.01) | |
| *C09J 201/02* | (2006.01) | |

(52) U.S. Cl.
CPC ............ *A61F 13/58* (2013.01); *A61F 13/581* (2013.01); *A61F 13/62* (2013.01); *B32B 7/04* (2013.01); *B32B 7/05* (2019.01); *B32B 27/00* (2013.01); *C09J 7/20* (2018.01); *C09J 201/00* (2013.01); *B32B 5/022* (2013.01); *B32B 27/12* (2013.01); *B32B 27/20* (2013.01); *B32B 27/302* (2013.01); *B32B 27/304* (2013.01); *B32B 27/32* (2013.01); *B32B 27/36* (2013.01); *B32B 2250/03* (2013.01); *B32B 2262/0253* (2013.01); *B32B 2405/00* (2013.01); *B32B 2555/02* (2013.01); *C09J 7/241* (2018.01); *C09J 201/02* (2013.01); *C09J 2301/30* (2020.08)

(58) Field of Classification Search
CPC ............... A61F 13/58; C09J 7/20; B32B 7/05
See application file for complete search history.

(56) References Cited

U.S. PATENT DOCUMENTS

| | | | |
|---|---|---|---|
| 4,237,890 A * | 12/1980 | Laplanche | .............. A61F 13/58 604/390 |
| 4,522,853 A | 6/1985 | Szonn et al. | |
| 4,787,897 A * | 11/1988 | Torimae | ............... C09J 153/025 604/389 |
| 5,807,371 A | 9/1998 | Toyoda et al. | |
| 6,063,838 A | 5/2000 | Hyde et al. | |
| 6,630,238 B2 | 10/2003 | Hyde et al. | |
| 6,632,522 B1 | 10/2003 | Hyde et al. | |
| 8,168,853 B2 | 5/2012 | Autran et al. | |
| 8,445,744 B2 | 5/2013 | Autran et al. | |
| 9,169,384 B2 | 10/2015 | Autran et al. | |
| 9,327,477 B2 | 5/2016 | Iyad et al. | |
| 9,549,902 B2 | 1/2017 | Stefanelli et al. | |
| 9,669,606 B2 | 6/2017 | Iyad et al. | |
| 9,895,275 B2 | 2/2018 | Autran et al. | |
| 10,500,107 B2 | 12/2019 | Autran et al. | |

(Continued)

FOREIGN PATENT DOCUMENTS

| | | |
|---|---|---|
| CN | 1671609 A | 9/2005 |
| CN | 101003043 A | 7/2007 |

(Continued)

OTHER PUBLICATIONS

Non-patent literature XP-002791498, dated 2017.

(Continued)

*Primary Examiner* — Anish P Desai
(74) *Attorney, Agent, or Firm* — Greenblum & Bernstein, P.L.C.

(57) ABSTRACT

Provided is an ultrasmall-sized fixing tape suitable for a disposal tape for an absorbent article, such as a disposable diaper, a sanitary napkin, or an incontinence pad. The ultrasmall fixing tape of the present invention includes: an extending portion; and a non-extending portion that is substantially free from extending, in which: the non-extending portion includes securing means in at least part thereof; the ultrasmall fixing tape has a base material layer B; the base material layer B has a thickness of 50 µm or more; and the base material layer B has an upper yield strength in a longitudinal direction thereof at a temperature of 23° C. and a humidity of 50% of from 5 N/25 mm to 15 N/25 mm.

25 Claims, 4 Drawing Sheets

(56) References Cited

U.S. PATENT DOCUMENTS

| | | |
|---|---|---|
| 2002/0007014 A1 | 1/2002 | Hyde et al. |
| 2007/0077418 A1 | 4/2007 | Sakurai et al. |
| 2007/0163705 A1 | 7/2007 | Dollase |
| 2008/0311332 A1 | 12/2008 | Sakurai et al. |
| 2009/0028929 A1 | 1/2009 | Stefanelli et al. |
| 2009/0258210 A1 | 10/2009 | Iyad et al. |
| 2009/0264844 A1 | 10/2009 | Autran et al. |
| 2010/0040826 A1 | 2/2010 | Autran et al. |
| 2011/0067799 A1 | 3/2011 | Mussig et al. |
| 2012/0184169 A1 | 7/2012 | Autran et al. |
| 2012/0301660 A1 | 11/2012 | Bartusiak |
| 2013/0202902 A1 | 8/2013 | Dejesus |
| 2013/0237938 A1 | 9/2013 | Autran et al. |
| 2014/0242360 A1 | 8/2014 | Iyad et al. |
| 2016/0015576 A1 | 1/2016 | Autran et al. |
| 2016/0159031 A1 * | 6/2016 | Ikishima ............ B32B 5/022 442/328 |
| 2017/0313034 A1 | 11/2017 | Takeda |
| 2017/0320300 A1 | 11/2017 | Takeda |
| 2017/0320304 A1 | 11/2017 | Takeda |

FOREIGN PATENT DOCUMENTS

| | | | |
|---|---|---|---|
| CN | 101977577 A | 2/2011 | |
| CN | 103476888 A | 12/2013 | |
| CN | 103582683 A | 2/2014 | |
| CN | 103906490 A | 7/2014 | |
| CN | 103957852 A | 7/2014 | |
| CN | 107000392 A | 8/2017 | |
| EP | 1692240 | 8/2006 | |
| JP | H09-099010 A | 4/1997 | |
| JP | H09-194801 A | 7/1997 | |
| JP | H09-316406 A | 12/1997 | |
| JP | H10-110145 A | 4/1998 | |
| JP | H11-152454 A | 6/1999 | |
| JP | H11-152455 A | 6/1999 | |
| JP | 2000-502385 A | 2/2000 | |
| JP | 2001-64602 | 3/2001 | |
| JP | 2003-153940 A | 5/2003 | |
| JP | 2003-311884 | 11/2003 | |
| JP | 2010-100038 A | 5/2010 | |
| JP | 2011-514178 A | 5/2011 | |
| JP | 2011-514391 A | 5/2011 | |
| JP | 2011-519989 A | 7/2011 | |
| JP | 2012-214698 A | 11/2012 | |
| JP | 2013-118923 A | 6/2013 | |
| JP | 2013-244127 A | 12/2013 | |
| JP | 2014-514390 A | 6/2014 | |
| JP | 2014-520173 A | 8/2014 | |
| JP | 2015-020317 A | 2/2015 | |
| RU | 2420269 | 6/2011 | |
| WO | 2013/086320 A1 | 6/2013 | |
| WO | WO-2013086320 A1 * | 6/2013 | ............ C09J 7/20 |
| WO | 2015/008595 | 1/2015 | |
| WO | WO-2015008595 A1 * | 1/2015 | ......... B32B 27/304 |

OTHER PUBLICATIONS

Extended European Search Report issued in corresponding European Patent Application No. 16857365.7, dated Jul. 2, 2019.
The Russian Office Action, Russian Patent Office, Application No. 2018118560, dated Jan. 31, 2020, with English translation.
International Search Report from Patent Application No. PCT/JP2016/080490, dated Jan. 10, 2017.
International Preliminary Report on Patentability from Patent Application No. PCT/JP2016/080490, dated Apr. 24, 2018.
Written Patent Opposition to the Japanese patent dated Aug. 19, 2020, filed against corresponding Japanese patent No. 6650730 and English translation thereof.
Chinese Office Action, Chinese Patent Office, Application No. 201680061663.1, dated May 29, 2020, English translation.
Office Action, Chinese Patent Office, in counterpart Chinese Application No. 201680061663.1, dated Jun. 16, 2021 (with English translation).
Lee Barber et al., "Validity and reliability of a simple ultrasound approach to measure medial gastrocnemius muscle length," Journal of Anatomy, Mar. 31, 2011, 218, pp. 637 to 642.

* cited by examiner

ULTRASMALL SECURING TAPE AND ARTICLE INCLUDING SAME

TECHNICAL FIELD

The present invention relates to an ultrasmall fixing tape and an article including the ultrasmall fixing tape.

BACKGROUND ART

The use of a fixing tape is given as one method of, for example, reducing the sizes of wastes and the like to dispose of the wastes and the like.

Typical examples of such fixing tape include disposal tapes for absorbent articles, such as a disposable diaper, a sanitary napkin, and an incontinence pad. Any such disposal tape has a structure in which one or a plurality of tapes are folded, and when the tape is extended, and is then bonded to a used absorbent article folded into a small size to be secured thereto, the tape suppresses the used absorbent article folded into a small size from returning to its original shape (see, for example, Patent Literatures 1 to 5).

The extension amount of each of the disposal tapes for absorbent articles, such as a disposable diaper, a sanitary napkin, and an incontinence pad, at the time of its extension has heretofore been insufficient. In addition, when any such tape is excessively extended, the tape ruptures, and hence it has been necessary to prepare a disposal tape having a certain size.

Meanwhile, in association with, for example, the advent of an aging society, there has been a growing demand for absorbent articles, and hence a reduction in cost for a disposal tape has been required.

CITATION LIST

Patent Literature

[PTL 1] JP 09-99010 A
[PTL 2] JP 09-194801 A
[PTL 3] JP 2003-153940 A
[PTL 4] JP 2013-118923 A
[PTL 5] JP 2013-244127 A

SUMMARY OF INVENTION

Technical Problem

The present invention has been made to solve the conventional problems, and an object of the present invention is to provide an ultrasmall-sized fixing tape suitable for a disposal tape for an absorbent article, such as a disposable diaper, a sanitary napkin, or an incontinence pad.

Solution to Problem

An ultrasmall fixing tape according to one embodiment of the present invention includes: an extending portion; and a non-extending portion that is substantially free from extending, in which: the non-extending portion includes securing means in at least part thereof; the ultrasmall fixing tape has a base material layer B; the base material layer B has a thickness of 50 µm or more; and the base material layer B has an upper yield strength in a longitudinal direction thereof at a temperature of 23° C. and a humidity of 50% of from 5 N/25 mm to 15 N/25 mm.

In one embodiment, the thickness of the base material layer B is from 50 µm to 125 µm.

In one embodiment, the upper yield strength is from 5 N/25 mm to 15 N/25 mm.

In one embodiment, the base material layer B has an extension at rupture in the longitudinal direction at a temperature of 23° C. and a humidity of 50% of 600% or more.

In one embodiment, the extension at rupture is from 600% to 1,500%.

In one embodiment, the base material layer B has a permanent strain amount of 30% or less when the base material layer B is extended in the longitudinal direction at an extension percentage of 400% and then returned to a steady state, subsequently extended in the longitudinal direction at an extension percentage of 100% and then returned to the steady state, and further extended in the longitudinal direction at an extension percentage of 100% at a temperature of 23° C. and a humidity of 50%.

In one embodiment, the permanent strain amount is from 5% to 30%.

In one embodiment, the extending portion includes an engaging portion in at least part thereof.

In one embodiment, the engaging portion has a shear adhesive strength at a temperature of 23° C. and a humidity of 50% of $6N/1.95 mm^2$ or more.

In one embodiment, the shear adhesive strength is from 6 $N/1.95 mm^2$ to 25 $N/1.95 mm^2$.

In one embodiment, the engaging portion includes a pressure-sensitive adhesive layer or a hook material.

In one embodiment, the securing means includes a pressure-sensitive adhesive.

In one embodiment, the pressure-sensitive adhesive includes a hot-melt pressure-sensitive adhesive.

In one embodiment, the ultrasmall fixing tape has a length in a longitudinal direction thereof of from 5 mm to 80 mm.

In one embodiment, the length in the longitudinal direction is from 10 mm to 50 mm.

In one embodiment, the ultrasmall fixing tape has a length in a widthwise direction thereof of from 5 mm to 40 mm.

In one embodiment, the length in the widthwise direction is from 5 mm to 20 mm.

In one embodiment, the base material layer B includes a stretchable laminate including an elastomer layer and an olefin-based resin layer arranged on at least one side of the elastomer layer.

In one embodiment, the olefin-based resin layer contains a non-elastomeric olefin-based resin.

In one embodiment, the non-elastomeric olefin-based resin contains an α-olefin homopolymer.

In one embodiment, the α-olefin homopolymer includes at least one kind selected from polyethylene (PE) and homopolypropylene (PP).

In one embodiment, the α-olefin homopolymer contains at least one kind selected from high-density polyethylene (HDPE) and homopolypropylene (PP).

In one embodiment, the elastomer layer contains an olefin-based elastomer.

In one embodiment, the olefin-based elastomer includes an α-olefin-based elastomer.

In one embodiment, the α-olefin-based elastomer includes at least one kind selected from an ethylene-based elastomer and a propylene-based elastomer.

In one embodiment, the α-olefin-based elastomer includes a metallocene-based α-olefin-based elastomer.

In one embodiment, the ultrasmall fixing tape of the present invention has a folding-processed portion in at least one site.

An absorbent article according to one embodiment of the present invention includes the ultrasmall fixing tape.

Advantageous Effects of Invention

According to the present invention, it is possible to provide the ultrasmall-sized fixing tape suitable for a disposal tape for an absorbent article, such as a disposable diaper, a sanitary napkin, or an incontinence pad.

DESCRIPTION OF EMBODIMENTS

<<Ultrasmall Fixing Tape>>

Figure 1:
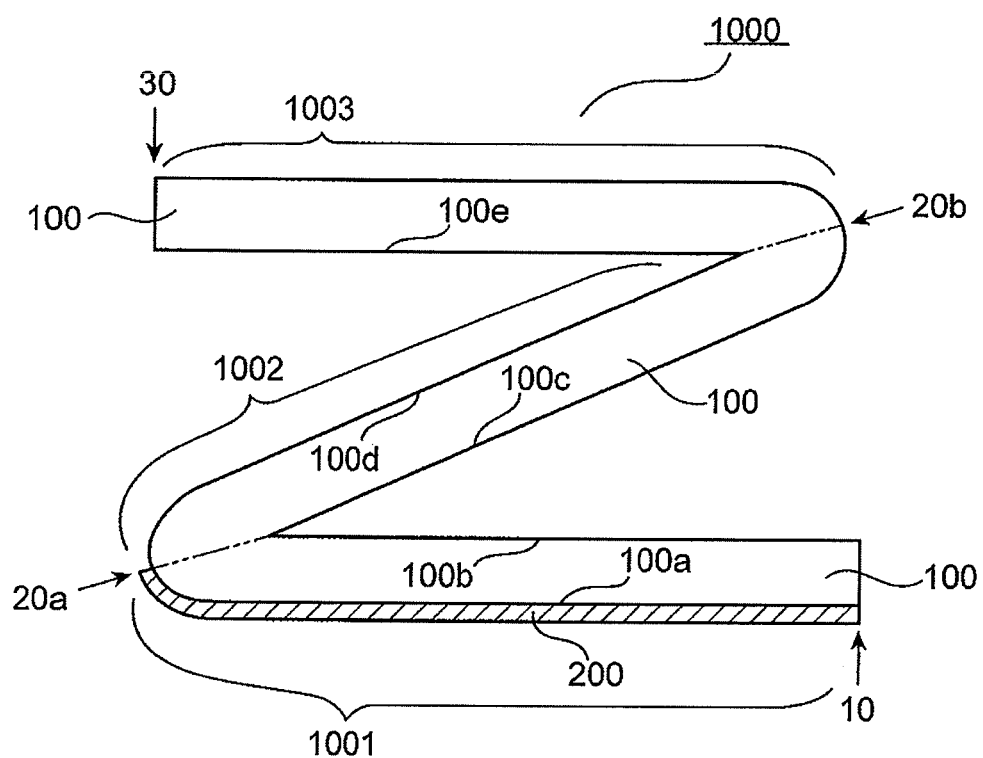
FIG. 1 is a schematic sectional view of an ultrasmall fixing tape according to one embodiment of the present invention.

An ultrasmall fixing tape of the present invention is an ultrasmall fixing tape including an extending portion and a non-extending portion that is substantially free from extending.

The ultrasmall fixing tape of the present invention is an ultrasmall-sized fixing tape.

The length of the ultrasmall fixing tape of the present invention in its longitudinal direction is preferably from 5 mm to 80 mm, more preferably from 10 mm to 70 mm, still more preferably from 15 mm to 65 mm, particularly preferably from 15 mm to 50 mm, most preferably from 15 mm to 40 mm. When the length in the longitudinal direction falls within the range, a further ultrasmall-sized fixing tape can be provided.

The length of the ultrasmall fixing tape of the present invention in its widthwise direction is preferably from 5 mm to 40 mm, more preferably from 5 mm to 35 mm, still more preferably from 5 mm to 30 mm, particularly preferably from 5 mm to 25 mm, most preferably from 5 mm to 20 mm. When the length in the widthwise direction falls within the range, a further ultrasmall-sized fixing tape can be provided.

In the ultrasmall fixing tape of the present invention, the non-extending portion includes securing means in at least part thereof. The ultrasmall fixing tape of the present invention can be secured to an adherend (e.g., an absorbent article) by the securing means. Details about the securing means are described later.

The ultrasmall fixing tape of the present invention has abase material layer B. The base material layer B may be only one layer, or may be a laminate of two or more layers. As described later, the base material layer B is preferably a stretchable laminate including an elastomer layer and an olefin-based resin layer arranged on at least one side of the elastomer layer.

As long as the ultrasmall fixing tape of the present invention has the base material layer B, the tape may have any appropriate other layer to the extent that the effects of the present invention are not impaired.

In the ultrasmall fixing tape of the present invention, the extending portion preferably includes an engaging portion in at least part thereof. Any appropriate engaging portion may be adopted as such engaging portion to the extent that the effects of the present invention are not impaired as long as the portion has such a function as to be capable of engaging with any other site. Such engaging portion is preferably a pressure-sensitive adhesive layer or a hook material. The engaging portion may be a portion in which the pressure-sensitive adhesive layer and the hook material coexist.

The ultrasmall fixing tape of the present invention preferably has a folding-processed portion in at least one site. When the ultrasmall fixing tape of the present invention has such folding-processed portion in one site, the tape has such a form as to be folded into a V shape. When the ultrasmall fixing tape of the present invention has such folding-processed portions in two sites, the tape has such a form as to be folded into, for example, a Z shape. When the ultrasmall fixing tape of the present invention has such folding-processed portions in three sites, the tape has such a form as to be folded into, for example, an M shape.

FIG. 1 is a schematic sectional view of an ultrasmall fixing tape according to one embodiment of the present invention. In FIG. 1, a case in which an ultrasmall fixing tape (1000) of the present invention has folding-processed portions in two sites is illustrated, and the ultrasmall fixing tape (1000) of the present invention has such a form as to be folded into a Z shape. The ultrasmall fixing tape (1000) of the present invention has a base material layer B (100).

In FIG. 1, a folding-processed portion V1 (20a) and a folding-processed portion V2 (20b) are arranged in the range of from one end portion E1 (10) to the other end portion E2 (30) in the longitudinal direction of the ultrasmall fixing tape (1000) of the present invention, and the tape is folded into the Z shape by the folding-processed portion V1 (20a) and the folding-processed portion V2 (20b). In FIG. 1, the range of from the end portion E1 (10) to the folding-processed portion V1 (20a) is a portion P1 (1001), the range of from the folding-processed portion V1 (20a) to the folding-processed portion V2 (20b) is a portion P2 (1002), and the range of from the folding-processed portion V2 (20b) to the end portion E2 (30) is a portion P3 (1003).

In FIG. 1, in the portion P1 (1001), securing means (200) is arranged on a surface a (100a) side of the base material layer B (100). The site in the portion P1 (1001) where the securing means (200) is arranged serves as a non-extending portion that is substantially free from extending because the site can be secured to an adherend (e.g., an absorbent article).

In FIG. 1, the portion P2 (1002) and the portion P3 (1003) serve as an extending portion. Specifically, for example, a state in which the tape is folded into the Z shape is developed by pulling the portion P3 (1003), and the portion P2 (1002) and the portion P3 (1003) are extended by further pulling the portion P3 (1003). The portion P3 (1003) serving as the extending portion can be secured to an adherend (e.g., an absorbent article) by any appropriate means (preferably an engaging portion to be described later). For example, the portion can be secured so that a used absorbent article folded into a small size may not open, and hence the used absorbent article folded into a small size can be suppressed from returning to its original shape.

In FIG. 1, any appropriate pressure-sensitive adhesive layer or release layer may be arranged on each of a surface b (100b) side of the base material layer B (100) in the portion P1 (1001), a surface c (100c) side of the base material layer B (100) in the portion P2 (1002), a surface d (100d) side of the base material layer B (100) in the portion P2 (1002), and a surface e (100*e*) side of the base material layer B (100) in the portion P3 (1003) so that the tape may be folded into the Z shape before its use, and a state in which the tape is folded into the Z shape may be developed at the time of the use.

The following embodiment is given as one embodiment: a release layer is arranged on the surface b (100*b*) side of the base material layer B (100) in the portion P1 (1001), a pressure-sensitive adhesive layer is arranged on the surface c (100*c*) side of the base material layer B (100) in the portion P2 (1002), a release layer is arranged on the surface d (100*d*) side of the base material layer B (100) in the portion P2 (1002), and a pressure-sensitive adhesive layer is arranged on the surface e (100*e*) side of the base material layer B (100) in the portion P3 (1003).

The following embodiment is given as another embodiment: no release layer is arranged on the surface b (100*b*) side of the base material layer B (100) in the portion P1 (1001), a pressure-sensitive adhesive layer is arranged on the surface c (100*c*) side of the base material layer B (100) in the portion P2 (1002), a release layer is arranged on the surface d (100*d*) side of the base material layer B (100) in the portion P2 (1002), and a pressure-sensitive adhesive layer is arranged on the surface e (100*e*) side of the base material layer B (100) in the portion P3 (1003). The pressure-sensitive adhesive layer to be arranged on the surface c (100*c*) side in this case is preferably, for example, such an olefin-based hot-melt pressure-sensitive adhesive as described later.

<Base Material Layer B>

The thickness of the base material layer B is 50 µm or more, preferably from 50 µm to 125 µm, more preferably from 50 µm to 110 µm, still more preferably from 50 µm to 100 µm, particularly preferably from 50 µm to 90 µm, most preferably from 50 µm to 80 µm. When the thickness of the base material layer B falls within the range, even in the case where the length of the ultrasmall fixing tape of the present invention in the longitudinal direction or widthwise direction is short, the tape can be easily extended and can be sufficiently ultrasmall-sized.

The upper yield strength of the base material layer B in its longitudinal direction at a temperature of 23° C. and a humidity of 50% is from 5 N/25 mm to 15 N/25 mm, preferably from 5 N/25 mm to 14 N/25 mm, more preferably from 5 N/25 mm to 13 N/25 mm, still more preferably from 5 N/25 mm to 12 N/25 mm, particularly preferably from 5 N/25 mm to 11 N/25 mm, most preferably from 5 N/25 mm to 10N/25 mm. When the upper yield strength of the base material layer B in the longitudinal direction at a temperature of 23° C. and a humidity of 50% falls within the range, even in the case where the length of the ultrasmall fixing tape of the present invention in the longitudinal direction or widthwise direction is short, the tape can be easily extended and can be sufficiently ultrasmall-sized. In addition, the tape can express such a strength as to be hard to rupture even when sufficiently extended.

The extension at rupture of the base material layer B in the longitudinal direction at a temperature of 23° C. and a humidity of 50% is preferably 600% or more, more preferably from 600% to 1,500%, still more preferably from 600% to 1,400%, particularly preferably from 600% to 1,300%, most preferably from 600% to 1,200%. When the extension at rupture of the base material layer B in the longitudinal direction at a temperature of 23° C. and a humidity of 50% falls within the range, even in the case where the length of the ultrasmall fixing tape of the present invention in the longitudinal direction or widthwise direction is short, the tape can be sufficiently extended without rupturing, and can be more sufficiently ultrasmall-sized.

The permanent strain amount of the base material layer B when the base material layer B is extended in the longitudinal direction at an extension percentage of 400% and then returned to a steady state, subsequently extended in the longitudinal direction at an extension percentage of 100% and then returned to the steady state, and further extended in the longitudinal direction at an extension percentage of 100% at a temperature of 23° C. and a humidity of 50% is preferably 30% or less, more preferably from 5% to 30%, still more preferably from 5% to 28%, particularly preferably from 5% to 25%, most preferably from 5% to 20%. The permanent strain amount is a permanent strain amount observed when the base material layer B is extended in the longitudinal direction at an extension percentage of 400% and then returned to the steady state (corresponding to an extension percentage of 0%) once, subsequently extended in the longitudinal direction at an extension percentage of 100% and then returned to the steady state (corresponding to an extension percentage of 0%) again, and further extended in the longitudinal direction at an extension percentage of 100%, and the permanent strain amount reflects that the ultrasmall fixing tape of the present invention has sufficient elastic recoverability even after its sufficient extension. When the permanent strain amount falls within the range, the ultrasmall fixing tape of the present invention can express sufficient elastic recoverability and hence can exhibit a satisfactory fitting feeling even after the sufficient extension. More specifically, for example, when the ultrasmall fixing tape of the present invention is sufficiently extended and secured so that a used absorbent article folded into a small size may not open, elastic recoverability that enables the ultrasmall fixing tape of the present invention to return from the extended state in the site where the tape is secured can be reliably expressed without the loosening of the securing, and hence the used absorbent article folded into a small size can be suppressed from returning to its original shape.

The base material layer B preferably has the same composition throughout the entirety of the ultrasmall fixing tape of the present invention. In this case, the production of the ultrasonic fixing tape of the present invention can be simplified, and hence cost for the production can be reduced.

The base material layer B may be only one layer, or may be a laminate of two or more layers.

Any appropriate layer may be adopted as the base material layer B to the extent that the effects of the present invention are not impaired. Such base material layer B is preferably a stretchable laminate including an elastomer layer and an olefin-based resin layer arranged on at least one side of the elastomer layer.

A stretchable laminate according to a preferred mode of the base material layer B includes an elastomer layer and an olefin-based resin layer arranged on at least one side of the elastomer layer. That is, in the stretchable laminate, the olefin-based resin layer may be arranged only on one side of the elastomer layer, or the olefin-based resin layer may be arranged on each of both sides of the elastomer layer. When the stretchable laminate has such construction, even in the case where the length of the ultrasmall fixing tape of the present invention in the longitudinal direction or widthwise direction is short, the tape can be more easily extended without rupturing, and can be more sufficiently ultrasmall-sized. In addition, the tape can express such a strength as to be harder to rupture even when sufficiently extended, and the tape can express more sufficient elastic recoverability and hence can exhibit a more satisfactory fitting feeling even after its sufficient extension.

The stretchable laminate may include any appropriate other layer to the extent that the effects of the present invention are not impaired. The number of such any appropriate other layers may be only one, or may be two or more.

In the stretchable laminate, it is preferred that the olefin-based resin layer be directly laminated on the elastomer layer. That is, one preferred embodiment of the stretchable laminate is a mode in which the olefin-based resin layer is directly laminated on at least one side of the elastomer layer. When the olefin-based resin layer is directly laminated on the elastomer layer as described above, even in the case where the length of the ultrasmall fixing tape of the present invention in the longitudinal direction or widthwise direction is short, the tape can be even more easily extended without rupturing, and can be even more sufficiently ultrasmall-sized. In addition, the tape can express such a strength as to be even harder to rupture even when sufficiently extended, and the tape can express even more sufficient elastic recoverability and hence can exhibit an even more satisfactory fitting feeling even after its sufficient extension.

Figure 2:
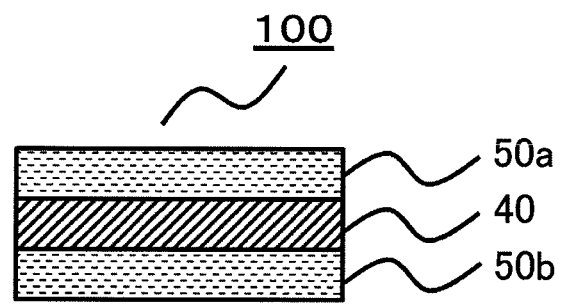
FIG. 2 is a schematic sectional view of a stretchable laminate according to a preferred mode of a base material layer B.

FIG. 2 is a schematic cross-sectional view of a stretchable laminate according to a preferred mode of the base material layer B. A base material layer B (100) that is a stretchable laminate illustrated in FIG. 2 includes an elastomer layer (40), an olefin-based resin layer (50a) arranged on one side of the elastomer layer (40), and an olefin-based resin layer (50b) arranged on the elastomer layer (40) on an opposite side to the olefin-based resin layer (50a). A material for bonding the elastomer layer (40) and the olefin-based resin layer (50a) and/or for bonding the elastomer layer (40) and the olefin-based resin layer (50b) may be present therebetween. Examples of such material include an adhesive, a pressure-sensitive adhesive, and a hot-melt pressure-sensitive adhesive.

Any appropriate number may be adopted as the number of the elastomer layers. The number of such elastomer layers is preferably from 1 to 5, more preferably from 1 to 3, still more preferably 1 or 2, particularly preferably 1.

When the number of the elastomer layers is two or more, all of the respective layers may be layers of the same kind, or at least two of the layers may be layers of different kinds.

The elastomer layer may contain any appropriate resin to the extent that the effects of the present invention are not impaired. Examples of such resin include an olefin-based elastomer and a styrene-based elastomer. The elastomer layer preferably contains the olefin-based elastomer. When the elastomer layer contains the olefin-based elastomer, even in the case where the length of the ultrasmall fixing tape of the present invention in the longitudinal direction or widthwise direction is short, the tape can be even more easily extended without rupturing, and can be even more sufficiently ultrasmall-sized. In addition, the tape can express such a strength as to be even harder to rupture even when sufficiently extended, and the tape can express even more sufficient elastic recoverability and hence can exhibit an even more satisfactory fitting feeling even after its sufficient extension.

The olefin-based elastomer may be only one kind of elastomer, or may be a blend of two or more kinds of elastomers.

When the elastomer layer contains the olefin-based elastomer, steps in the production of the elastomer layer can be simplified, and hence processing cost can be suppressed. This is because of the following reason: when the olefin-based elastomer is adopted, extrusion molding can be performed by using fewer kinds of resins in the production of the elastomer layer, and hence the need for the production of a master batch can be eliminated.

The content of the olefin-based elastomer in the elastomer layer is preferably from 50 wt % to 100 wt %, more preferably from 70 wt % to 100 wt %, still more preferably from 80 wt % to 100 wt %, particularly preferably from 90 wt % to 100 wt %, most preferably from 95 wt % to 100 wt % because the effects of the present invention are expressed to a larger extent. When the content of the olefin-based elastomer in the elastomer layer falls within the range, even in the case where the length of the ultrasmall fixing tape of the present invention in the longitudinal direction or widthwise direction is short, the tape can be even more easily extended without rupturing, and can be even more sufficiently ultrasmall-sized. In addition, the tape can express such a strength as to be even harder to rupture even when sufficiently extended, and the tape can express even more sufficient elastic recoverability and hence can exhibit an even more satisfactory fitting feeling even after its sufficient extension.

Examples of the olefin-based elastomer include an olefin block copolymer, an olefin random copolymer, an ethylene copolymer, a propylene copolymer, an ethylene olefin block copolymer, a propylene olefin block copolymer, an ethylene olefin random copolymer, a propylene olefin random copolymer, an ethylene propylene random copolymer, an ethylene (1-butene) random copolymer, an ethylene (1-pentene) olefin block copolymer, an ethylene (1-hexene) random copolymer, an ethylene (1-heptene) olefin block copolymer, an ethylene (1-octene) olefin block copolymer, an ethylene (1-nonene) olefin block copolymer, an ethylene (1-decene) olefin block copolymer, a propylene ethylene olefin block copolymer, an ethylene ($\alpha$-olefin) copolymer, an ethylene ($\alpha$-olefin) random copolymer, an ethylene ($\alpha$-olefin) block copolymer, and combinations thereof.

The olefin-based elastomer has a density of preferably from 0.890 g/cm$^3$ to 0.830 g/cm$^3$, more preferably from 0.888 g/cm$^3$ to 0.835 g/cm$^3$, still more preferably from 0.886 g/cm$^3$ to 0.835 g/cm$^3$, particularly preferably from 0.885 g/cm$^3$ to 0.840 g/cm$^3$, most preferably from 0.885 g/cm$^3$ to 0.845 g/cm$^3$. When the olefin-based elastomer whose density falls within the range is incorporated into the elastomer layer, even in the case where the length of the ultrasmall fixing tape of the present invention in the longitudinal direction or widthwise direction is short, the tape can be even more easily extended without rupturing, and can be even more sufficiently ultrasmall-sized. In addition, the tape can express such a strength as to be even harder to rupture even when sufficiently extended, and the tape can express even more sufficient elastic recoverability and hence can exhibit an even more satisfactory fitting feeling even after its sufficient extension.

The olefin-based elastomer has a MFR at 230° C. and 2.16 kgf of preferably from 1.0 g/10 min to 25.0 g/10 min, more preferably from 2.0 g/10 min to 23.0 g/10 min, still more preferably from 2.0 g/10 min to 21.0 g/10 min, particularly preferably from 2.0 g/10 min to 20.0 g/10 min, most preferably from 2.0 g/10 min to 19.0 g/10 min. When the olefin-based elastomer whose MFR falls within the range is incorporated into the elastomer layer, even in the case where the length of the ultrasmall fixing tape of the present invention in the longitudinal direction or widthwise direction is short, the tape can be even more easily extended without rupturing, and can be even more sufficiently ultrasmall-sized. In addition, the tape can express such a strength as to be even harder to rupture even when sufficiently extended, and the tape can express even more sufficient elastic recoverability and hence can exhibit an even more satisfactory fitting feeling even after its sufficient extension.

The olefin-based elastomer is specifically preferably an α-olefin-based elastomer, that is, a copolymer of two or more kinds of α-olefins having an elastomer characteristic. Of such α-olefin-based elastomers, at least one kind selected from an ethylene-based elastomer, a propylene-based elastomer, and a 1-butene-based elastomer is more preferred. When such α-olefin-based elastomer is adopted as the olefin-based elastomer, even in the case where the length of the ultrasmall fixing tape of the present invention in the longitudinal direction or widthwise direction is short, the tape can be even more easily extended without rupturing, and can be even more sufficiently ultrasmall-sized. In addition, the tape can express such a strength as to be even harder to rupture even when sufficiently extended, and the tape can express even more sufficient elastic recoverability and hence can exhibit an even more satisfactory fitting feeling even after its sufficient extension.

Of the α-olefin-based elastomers, an ethylene-based elastomer or a propylene-based elastomer is particularly preferred. When the ethylene-based elastomer or the propylene-based elastomer is adopted as the olefin-based elastomer, even in the case where the length of the ultrasmall fixing tape of the present invention in the longitudinal direction or widthwise direction is short, the tape can be even more easily extended without rupturing, and can be even more sufficiently ultrasmall-sized. In addition, the tape can express such a strength as to be even harder to rupture even when sufficiently extended, and the tape can express even more sufficient elastic recoverability and hence can exhibit an even more satisfactory fitting feeling even after its sufficient extension.

The α-olefin-based elastomer is also available as a commercial product. Examples of such commercial product include some products in the "Tafmer" (trademark) series (e.g., Tafmer PN-3560) manufactured by Mitsui Chemicals, Inc., and some products in the "Vistamaxx" (trademark) series (e.g., Vistamaxx 6202 and Vistamaxx 7010) manufactured by Exxon Mobil Corporation.

The α-olefin-based elastomer is preferably a metallocene-based α-olefin-based elastomer produced by using a metallocene catalyst. When the metallocene-based α-olefin-based elastomer is adopted, even in the case where the length of the ultrasmall fixing tape of the present invention in the longitudinal direction or widthwise direction is short, the tape can be even more easily extended without rupturing, and can be even more sufficiently ultrasmall-sized. In addition, the tape can express such a strength as to be even harder to rupture even when sufficiently extended, and the tape can express even more sufficient elastic recoverability and hence can exhibit an even more satisfactory fitting feeling even after its sufficient extension.

The elastomer layer may contain any appropriate other component as long as the effects of the present invention are not impaired. Examples of such other component include any other polymer, a tackifier, a plasticizer, an antidegradant, a pigment, a dye, an antioxidant, an antistatic agent, a lubricant, a foaming agent, a heat stabilizer, a light stabilizer, an inorganic filler, and an organic filler. The number of kinds of those components may be only one, or may be two or more. The content of the other component in the elastomer layer is preferably 10 wt % or less, more preferably 7 wt % or less, still more preferably 5 wt % or less, particularly preferably 2 wt % or less, most preferably 1 wt % or less.

The thickness of the elastomer layer is preferably from 8 μm to 450 μm, more preferably from 8 μm to 220 μm, still more preferably from 8 μm to 180 μm, particularly preferably from 8 μm to 90 μm, most preferably from 8 μm to 67 μm. When the thickness of the elastomer layer is adjusted to fall within such range, a stretchable laminate having more excellent fittability can be provided.

Any appropriate number may be adopted as the number of the olefin-based resin layers. The number of such olefin-based resin layers is preferably from 1 to 5, more preferably from 1 to 3, still more preferably 1 or 2, particularly preferably 2 (e.g., one olefin-based resin layer is arranged on each of both sides of the elastomer layer).

When the number of the olefin-based resin layers is two or more, all of the respective layers may be layers of the same kind, or at least two of the layers may be layers of different kinds.

The olefin-based resin layer may contain any appropriate resin to the extent that the effects of the present invention are not impaired. The olefin-based resin layer preferably contains a non-elastomeric olefin-based resin. The non-elastomeric olefin-based resin means an olefin-based resin that is not an elastomeric olefin-based resin. When the olefin-based resin layer contains the non-elastomeric olefin-based resin, even in the case where the length of the ultrasmall fixing tape of the present invention in the longitudinal direction or widthwise direction is short, the tape can be even more easily extended without rupturing, and can be even more sufficiently ultrasmall-sized. In addition, the tape can express such a strength as to be even harder to rupture even when sufficiently extended, and the tape can express even more sufficient elastic recoverability and hence can exhibit an even more satisfactory fitting feeling even after its sufficient extension.

The non-elastomeric olefin-based resin may be only one kind of resin, or may be a blend or copolymer of two or more kinds of resins.

The content of the non-elastomeric olefin-based resin in the olefin-based resin layer is preferably from 50 wt % to 100 wt %, more preferably from 70 wt % to 100 wt %, still more preferably from 80 wt % to 100 wt %, particularly preferably from 90 wt % to 100 wt %, most preferably from 95 wt % to 100 wt % because the effects of the present invention are expressed to a larger extent. When the content of the non-elastomeric olefin-based resin in the olefin-based resin layer falls within the range, even in the case where the length of the ultrasmall fixing tape of the present invention in the longitudinal direction or widthwise direction is short, the tape can be even more easily extended without rupturing, and can be even more sufficiently ultrasmall-sized. In addition, the tape can express such a strength as to be even harder to rupture even when sufficiently extended, and the tape can express even more sufficient elastic recoverability and hence can exhibit an even more satisfactory fitting feeling even after its sufficient extension.

Examples of the non-elastomeric olefin-based resin include an α-olefin homopolymer, a copolymer of two or more kinds of α-olefins, block polypropylene, random polypropylene, and a copolymer of one or two or more kinds of α-olefins and any other vinyl monomer. A copolymerization form in any such copolymer is, for example, a block form or a random form.

Examples of the α-olefin include α-olefins each having 2 to 12 carbon atoms. Examples of such α-olefin include ethylene, propylene, 1-butene, and 4-methyl-1-pentene.

Examples of the α-olefin homopolymer include polyethylene (PE), homopolypropylene (PP), poly(1-butene), and poly(4-methyl-1-pentene).

Examples of the polyethylene (PE) include low-density polyethylene (LDPE), linear low-density polyethylene (LLDPE), medium-density polyethylene (MDPE), and high-density polyethylene (HDPE).

The structure of the homopolypropylene (PP) may be any one of isotactic, atactic, and syndiotactic structures.

The non-elastomeric olefin-based resin preferably contains the α-olefin homopolymer, more preferably contains at least one kind selected from polyethylene (PE) and homopolypropylene (PP), and still more preferably contains at least one kind selected from high-density polyethylene (HDPE) and homopolypropylene (PP) because the effects of the present invention can be expressed to a larger extent. When the non-elastomeric olefin-based resin contains at least one kind selected from the high-density polyethylene (HDPE) and the homopolypropylene (PP), even in the case where the length of the ultrasmall fixing tape of the present invention in the longitudinal direction or widthwise direction is short, the tape can be even more easily extended without rupturing, and can be even more sufficiently ultrasmall-sized. In addition, the tape can express such a strength as to be even harder to rupture even when sufficiently extended, and the tape can express even more sufficient elastic recoverability and hence can exhibit an even more satisfactory fitting feeling even after its sufficient extension. The content of the α-olefin homopolymer in the non-elastomeric olefin-based resin is preferably from 50 wt % to 100 wt %, more preferably from 70 wt % to 100 wt %, still more preferably from 80 wt % to 100 wt %, still further more preferably from 90 wt % to 100 wt %, particularly preferably from 95 wt % to 100 wt %, most preferably substantially 100 wt % because the effects of the present invention can be expressed to a larger extent.

Examples of the copolymer of two or more kinds of α-olefins include an ethylene/propylene copolymer, an ethylene/1-butene copolymer, an ethylene/propylene/1-butene copolymer, a copolymer of ethylene/α-olefin having 5 to 12 carbon atoms, and a copolymer of propylene/α-olefin having 5 to 12 carbon atoms.

Examples of the copolymer of one or two or more kinds of α-olefins and any other vinyl monomer include an ethylene/vinyl acetate copolymer, an ethylene/acrylic acid alkyl ester copolymer, an ethylene/methacrylic acid alkyl ester copolymer, and an ethylene-non-conjugated diene copolymer.

A commercial product may be used as the non-elastomeric olefin-based resin.

The olefin-based resin layer may contain any appropriate other component to the extent that the effects of the present invention are not impaired. Examples of such other component include a releasing agent, a UV absorber, a heat stabilizer, a filler, a lubricant, a colorant (e.g., a dye), an antioxidant, an anti-build up agent, an anti-blocking agent, a foaming agent, and polyethyleneimine. Those components may be used alone or in combination thereof. The content of the other component in the olefin-based resin layer is preferably 10 wt % or less, more preferably 7 wt % or less, still more preferably 5 wt % or less, particularly preferably 2 wt % or less, most preferably 1 wt % or less.

Examples of the releasing agent include a fatty acid amide-based releasing agent, a silicone-based releasing agent, a fluorine-based releasing agent, and a long-chain alkyl-based releasing agent. Of those, a fatty acid amide-based releasing agent is preferred from the viewpoint that a peeling layer more excellent in balance between peelability and resistance against contamination due to bleedout can be formed, and a saturated fatty acid bisamide is more preferred. Any appropriate content may be adopted as the content of the releasing agent. Typically, the content is preferably from 0.01 wt % to 5 wt % with respect to a resin component (preferably the non-elastomeric olefin-based resin) in the olefin-based resin layer.

Examples of the UV absorber include a benzotriazole-based compound, a benzophenone-based compound, and a benzoate-based compound. Any appropriate content may be adopted as the content of the UV absorber as long as the UV absorber does not bleed out at the time of the forming. Typically, the content is preferably from 0.01 wt % to 5 wt % with respect to the resin component (preferably the non-elastomeric olefin-based resin) in the olefin-based resin layer.

Examples of the heat stabilizer include a hindered amine-based compound, a phosphorus-based compound, and a cyanoacrylate-based compound. Any appropriate content may be adopted as the content of the heat stabilizer as long as the heat stabilizer does not bleed out at the time of the forming. Typically, the content is preferably from 0.01 wt % to 5 wt % with respect to the resin component (preferably the non-elastomeric olefin-based resin) in the olefin-based resin layer.

Examples of the filler include inorganic fillers, such as talc, titanium oxide, calcium oxide, magnesium oxide, zinc oxide, titanium oxide, calcium carbonate, silica, clay, mica, barium sulfate, whisker, and magnesium hydroxide. The average particle diameter of the filler is preferably from 0.1 μm to 20 μm. Any appropriate content may be adopted as the content of the filler. Typically, the content is preferably from 1 wt % to 200 wt % with respect to the resin component (preferably the non-elastomeric olefin-based resin) in the olefin-based resin layer.

The thickness of the olefin-based resin layer is preferably from 2 μm to 50 μm, more preferably from 2 μm to 30 μm, still more preferably from 2 μm to 20 μm, particularly preferably from 2 μm to 10 μm, most preferably from 2 μm to 8 μm. When the thickness of the olefin-based resin layer falls within such range, even in the case where the length of the ultrasmall fixing tape of the present invention in the longitudinal direction or widthwise direction is short, the tape can be even more easily extended without rupturing, and can be even more sufficiently ultrasmall-sized. In addition, the tape can express such a strength as to be even harder to rupture even when sufficiently extended, and the tape can express even more sufficient elastic recoverability and hence can exhibit an even satisfactory fitting feeling even after its sufficient extension.

Any appropriate method may be adopted as a method of producing the stretchable laminate to the extent that the effects of the present invention are not impaired as long as such a construction that the olefin-based resin layer is arranged on at least one side of the elastomer layer can be built by the method.

The method of producing the stretchable laminate is typically, for example, a production method involving molding a laminate with a multilayer extrusion T-die molding machine. For example, when a stretchable laminate formed of a laminated construction "olefin-based resin layer/elastomer layer/olefin-based resin layer" is produced, a molding material for the olefin-based resin layer, a molding material for the elastomer layer, and a molding material for the other olefin-based resin layer are co-extruded from a T-die by using a three-layer extrusion T-die molding machine to be integrated, and are then wound in a roll shape. Thus, a rolled body of the stretchable laminate can be produced. In addition to the T-die method involving using the T-die, an inflation method or the like may also be adopted.

<Securing Means>

The thickness of the securing means is preferably from 40 μm to 150 μm, more preferably from 40 μm to 120 μm, still more preferably from 40 μm to 110 μm, particularly preferably from 40 μm to 100 μm, most preferably from 40 μm to 90 μm. When the thickness of the securing means falls within the range, the ultrasmall fixing tape of the present invention can be sufficiently secured to an adherend even in, for example, the case where the extending portion is sufficiently extended.

The securing means is included in at least part of the non-extending portion. The ultrasmall fixing tape of the present invention can be secured to an adherend (e.g., an absorbent article) by the securing means.

Any appropriate means may be adopted as the securing means to the extent that the effects of the present invention are not impaired as long as the ultrasmall fixing tape of the present invention can be secured to an adherend (e.g., an absorbent article) by the means. Such securing means is preferably a pressure-sensitive adhesive, more preferably a hot-melt pressure-sensitive adhesive.

Examples of a material for the pressure-sensitive adhesive serving as the securing means include an olefin-based resin, an acrylic resin, and a styrene-based thermoplastic elastomer. Those materials may be used alone or in combination thereof.

Preferred examples of the styrene-based thermoplastic elastomer include a hydrogenated styrene-butadiene rubber (HSBR), and a styrene-based block copolymer or a hydrogenated product thereof.

Examples of the styrene-based block copolymer include: styrene-based ABA-type block copolymers (triblock copolymers), such as a styrene-butadiene-styrene copolymer (SBS) and a styrene-isoprene-styrene copolymer (SIS); styrene-based ABAB-type block copolymers (tetrablock copolymers), such as a styrene-butadiene-styrene-butadiene copolymer (SBSB) and a styrene-isoprene-styrene-isoprene copolymer (SISI); styrene-based ABABA-type block copolymers (pentablock copolymers), such as a styrene-butadiene-styrene-butadiene-styrene copolymer (SBSBS) and a styrene-isoprene-styrene-isoprene-styrene copolymer (SISIS); and styrene-based block copolymers having more AB repeating units. Of those, styrene-based ABA-type block copolymers (triblock copolymers), such as a styrene-butadiene-styrene copolymer (SBS) and a styrene-isoprene-styrene copolymer (SIS), are each preferred as the styrene-based block copolymer, and a styrene-isoprene-styrene copolymer (SIS) is more preferred. When the material for the pressure-sensitive adhesive serving as the securing means contains the styrene-isoprene-styrene copolymer (SIS), the ultrasmall fixing tape of the present invention can be more sufficiently secured to an adherend even in, for example, the case where the extending portion is sufficiently extended.

Examples of the hydrogenated product of the styrene-based block copolymer include a styrene-ethylene-butylene copolymer-styrene copolymer (SEBS), a styrene-ethylene-propylene copolymer-styrene copolymer (SEPS), and a copolymer of a styrene-ethylene-butylene copolymer-styrene-ethylene-butylene copolymer (SEBSEB).

The material for the pressure-sensitive adhesive serving as the securing means may contain any other styrene-based thermoplastic elastomer to the extent that the effects of the present invention are not impaired. Examples of the other styrene-based thermoplastic elastomer include: styrene-based block copolymers except the above-mentioned styrene-based block copolymers; AB-type block polymers, such as a styrene-butadiene copolymer (SB), a styrene-isoprene copolymer (SI), a copolymer of a styrene-ethylene-butylene copolymer (SEB), and a copolymer of a styrene-ethylene-propylene copolymer (SEP); styrene-based random copolymers, such as a styrene-butadiene rubber (SBR); A-B—C-type styrene-olefin crystal-based block polymers, such as a copolymer of a styrene-ethylene-butylene copolymer-olefin crystal (SEBC); and hydrogenated products thereof. The other styrene-based thermoplastic elastomers may be used alone or in combination thereof.

In the material for the pressure-sensitive adhesive serving as the securing means, an additive, such as a tackifier, a softener, a polyolefin-based resin, a silicone-based polymer, a liquid acrylic copolymer, a phosphoric acid ester-based compound, an age inhibitor, a light stabilizer, a UV absorber, a surface lubricant, a leveling agent, a plasticizer, a low-molecular weight polymer, an antioxidant, a corrosion inhibitor, a polymerization inhibitor, a silane coupling agent, an inorganic or organic filler (e.g., calcium oxide, magnesium oxide, silica, zinc oxide, or titanium oxide), metal powder, a colorant, a pigment, or a heat stabilizer, may be appropriately added as required for the purpose of, for example, pressure-sensitive adhesive characteristic control.

The material for the pressure-sensitive adhesive serving as the securing means preferably contains a tackifier for the purpose of, for example, pressure-sensitive adhesive characteristic control.

Examples of the tackifier include a hydrocarbon-based tackifier, a terpene-based tackifier, a rosin-based tackifier, a phenol-based tackifier, an epoxy-based tackifier, a polyamide-based tackifier, an elastomer-based tackifier, and a ketone-based tackifier. The tackifiers may be used alone or in combination thereof.

Examples of the hydrocarbon-based tackifier include an aliphatic hydrocarbon resin, an aromatic hydrocarbon resin (e.g., a xylene resin), an aliphatic cyclic hydrocarbon resin, an aliphatic-aromatic petroleum resin (e.g., a styrene-olefin-based copolymer), an aliphatic-alicyclic petroleum resin, a hydrogenated hydrocarbon resin, a coumarone-based resin, and a coumarone-indene-based resin.

Examples of the terpene-based tackifier include: terpene-based resins, such as an α-pinene polymer and a β-pinene polymer; and modified terpene-based resins obtained by modification (e.g., phenol modification, aromatic modification, or hydrogenation modification) of the terpene-based resins (e.g., a terpene-phenol-based resin, a styrene-modified terpene-based resin, and a hydrogenated terpene-based resin).

Examples of the rosin-based tackifier include: unmodified rosins (raw rosins), such as gum rosin and wood rosin; modified rosins (e.g., hydrogenated rosin, disproportionated rosin, polymerized rosin, and other chemically modified rosins) obtained by modifying those unmodified rosins by hydrogenation, disproportionation, polymerization, and the like; and various other rosin derivatives.

Examples of the phenol-based tackifier include resol-type or novolac-type alkyl phenols.

The tackifier may be a tackifier commercially available as a blend with an olefin resin or a thermoplastic elastomer.

The surface of the pressure-sensitive adhesive serving as the securing means may be subjected to a surface treatment intended for pressure-sensitive adhesive property control, bonding workability, or the like, such as a corona discharge treatment, a UV irradiation treatment, a flame treatment, a plasma treatment, or a sputter etching treatment, as required.

A separator or the like may be temporarily bonded to the surface of the pressure-sensitive adhesive serving as the securing means to protect the pressure-sensitive adhesive as required until the pressure-sensitive adhesive is put into practical use.

<Pressure-Sensitive Adhesive Layer>

As described in FIG. 1, for example, any appropriate pressure-sensitive adhesive layer may be arranged on each of a surface b (100b) side of the base material layer B (100) in the portion P1 (1001), a surface c (100c) side of the base material layer B (100) in the portion P2 (1002), a surface d (100d) side of the base material layer B (100) in the portion P2 (1002), and a surface e (100e) side of the base material layer B (100) in the portion P3 (1003) so that the tape may be folded into the Z shape before its use, and a state in which the tape is folded into the Z shape may be developed at the time of the use.

The thickness of the pressure-sensitive adhesive layer is preferably from 40 µm to 150 µm, more preferably from 40 mm to 120 µm, still more preferably from 40 µm to 110 µm, particularly preferably from 40 µm to 100 µm, most preferably from 40 µm to 90 µm. When the thickness of the pressure-sensitive adhesive layer falls within the range, a state in which the ultrasmall fixing tape of the present invention is folded into a Z shape is easily maintained, and the state in which the tape is folded into the Z shape is easily developed at the time of its use. In addition, even in the case where the length of the tape in the longitudinal direction or widthwise direction is short, the tape can be more easily extended without rupturing, and can be more sufficiently ultrasmall-sized. In addition, the tape can express such a strength as to be harder to rupture even when sufficiently extended, and the tape can express more sufficient elastic recoverability and hence can exhibit a more satisfactory fitting feeling even after its sufficient extension.

The pressure-sensitive adhesive layer may be only one layer, or may be a laminate of two or more layers.

The pressure-sensitive adhesive layer is formed of any appropriate material to the extent that the effects of the present invention are not impaired. Examples of such material include olefin-based resins, acrylic resins, and styrene-based resins, such as a styrene-based thermoplastic elastomer. Those materials may be used alone or in combination thereof. Such material is preferably a hot-melt pressure-sensitive adhesive. Preferred specific examples of such material include an olefin-based hot-melt pressure-sensitive adhesive containing an olefin-based resin as a raw material, an acrylic hot-melt pressure-sensitive adhesive containing an acrylic resin as a raw material, and a styrene-based hot-melt pressure-sensitive adhesive containing a styrene-based resin, such as a styrene-based thermoplastic elastomer, as a raw material.

Preferred examples of the styrene-based thermoplastic elastomer include a hydrogenated styrene-butadiene rubber (HSBR), and a styrene-based block copolymer or a hydrogenated product thereof.

Examples of the styrene-based block copolymer include: styrene-based ABA-type block copolymers (triblock copolymers), such as a styrene-butadiene-styrene copolymer (SBS) and a styrene-isoprene-styrene copolymer (SIS); styrene-based ABAB-type block copolymers (tetrablock copolymers), such as a styrene-butadiene-styrene-butadiene copolymer (SBSB) and a styrene-isoprene-styrene-isoprene copolymer (SISI); styrene-based ABABA-type block copolymers (pentablock copolymers), such as a styrene-butadiene-styrene-butadiene-styrene copolymer (SBSBS) and a styrene-isoprene-styrene-isoprene-styrene copolymer (SISIS); and styrene-based block copolymers having more AB repeating units. Of those, styrene-based ABA-type block copolymers (triblock copolymers), such as a styrene-butadiene-styrene copolymer (SBS) and a styrene-isoprene-styrene copolymer (SIS), are each preferred as the styrene-based block copolymer, and a styrene-isoprene-styrene copolymer (SIS) is more preferred. When the pressure-sensitive adhesive layer contains the styrene-isoprene-styrene copolymer (SIS), a state in which the ultrasmall fixing tape of the present invention is folded into a Z shape is easily maintained, and the state in which the tape is folded into the Z shape is easily developed at the time of its use. In addition, even in the case where the length of the tape in the longitudinal direction or widthwise direction is short, the tape can be more easily extended without rupturing, and can be more sufficiently ultrasmall-sized. In addition, the tape can express such a strength as to be harder to rupture even when sufficiently extended, and the tape can express more sufficient elastic recoverability and hence can exhibit a more satisfactory fitting feeling even after its sufficient extension.

Examples of the hydrogenated product of the styrene-based block copolymer include a styrene-ethylene-butylene copolymer-styrene copolymer (SEBS), a styrene-ethylene-propylene copolymer-styrene copolymer (SEPS), and a copolymer of a styrene-ethylene-butylene copolymer-styrene-ethylene-butylene copolymer (SEBSEB).

The pressure-sensitive adhesive layer may contain any other styrene-based thermoplastic elastomer to the extent that the effects of the present invention are not impaired. Examples of the other styrene-based thermoplastic elastomer include: styrene-based block copolymers except the above-mentioned styrene-based block copolymers; AB-type block polymers, such as a styrene-butadiene copolymer (SB), a styrene-isoprene copolymer (SI), a copolymer of a styrene-ethylene-butylene copolymer (SEB), and a copolymer of a styrene-ethylene-propylene copolymer (SEP); styrene-based random copolymers, such as a styrene-butadiene rubber (SBR); A-B—C-type styrene-olefin crystal-based block polymers, such as a copolymer of a styrene-ethylene-butylene copolymer-olefin crystal (SEBC); and hydrogenated products thereof. The other styrene-based thermoplastic elastomers may be used alone or in combination thereof.

Any appropriate olefin-based hot-melt pressure-sensitive adhesive may be adopted as the olefin-based hot-melt pressure-sensitive adhesive to the extent that the effects of the present invention are not impaired.

Such olefin-based hot-melt pressure-sensitive adhesive preferably contains a Ziegler-Natta-based olefin resin, a hydrocarbon-based tackifier, and an oil component.

The Ziegler-Natta-based olefin resin is an olefin-based resin obtained by polymerization using a Ziegler-Natta catalyst. The Ziegler-Natta-based olefin resins may be used alone or in combination thereof.

Any appropriate olefin-based resin may be adopted as the Ziegler-Natta-based olefin resin to the extent that the effects of the present invention are not impaired as long as the olefin-based resin is obtained by polymerization using a Ziegler-Natta catalyst. Preferred examples of such Ziegler-Natta-based olefin resin include a homopolymer of an α-olefin and a copolymer of two or more kinds of α-olefins. The α-olefin is preferably an α-olefin having 2 to 20 carbon atoms. Examples of such α-olefin include ethylene, propylene, 1-butene, 1-pentene, 1-hexene, 1-heptene, 1-octene, and 4-methyl-1-pentene. The Ziegler-Natta-based olefin resin is more preferably a Ziegler-Natta-based olefin resin free of an aromatic structure. The adoption of the Ziegler-Natta-based olefin resin free of an aromatic structure can provide an olefin-based hot-melt pressure-sensitive adhesive more sufficiently suppressed in odor. The Ziegler-Natta-based olefin resin is preferably a propylene-α-olefin copolymer, more preferably a propylene-1-butene copolymer because the effects of the present invention can be more effectively expressed.

The content of the Ziegler-Natta-based olefin resin in the olefin-based hot-melt pressure-sensitive adhesive is preferably from 70 wt % to 20 wt %, more preferably from 65 wt % to 25 wt %, still more preferably from 60 wt % to 30 wt %, particularly preferably from 55 wt % to 35 wt % because the effects of the present invention can be more effectively expressed.

The Ziegler-Natta-based olefin resin is also available as a commercial product. Examples of such commercial product include some products in the "Rextac" (trademark) series (e.g., REXTAC RT 2788 and REXTAC RT 2730) manufactured by REXtac, LLC.

The olefin-based hot-melt pressure-sensitive adhesive may further contain a metallocene-based olefin resin. The metallocene-based olefin resin is an olefin-based resin obtained by polymerization using a metallocene catalyst. The metallocene-based olefin resins may be used alone or in combination thereof.

Any appropriate olefin-based resin may be adopted as the metallocene-based olefin resin to the extent that the effects of the present invention are not impaired as long as the olefin-based resin is obtained by polymerization using a metallocene catalyst. Preferred examples of such metallocene-based olefin resin include a homopolymer of an α-olefin and a copolymer of two or more kinds of α-olefins. The α-olefin is preferably an α-olefin having 2 to 20 carbon atoms. Examples of such α-olefin include ethylene, propylene, 1-butene, 1-pentene, 1-hexene, 1-heptene, 1-octene, and 4-methyl-1-pentene. The metallocene-based olefin resin is more preferably a metallocene-based olefin resin free of an aromatic structure. The adoption of the metallocene-based olefin resin free of an aromatic structure can provide an olefin-based hot-melt pressure-sensitive adhesive more sufficiently suppressed in odor. The metallocene-based olefin resin is preferably a propylene-based elastomer because the effects of the present invention can be more effectively expressed.

The content of the metallocene-based olefin resin in the olefin-based hot-melt pressure-sensitive adhesive is preferably from 20 wt % to 0 wt %, more preferably from 15 wt % to 0 wt %, still more preferably from 8 wt % to 0 wt %, yet still more preferably from 8 wt % to 0.1 wt %, particularly preferably from 5 wt % to 1 wt %, most preferably from 5 wt % to 2 wt %. When the content of the metallocene-based olefin resin in the olefin-based hot-melt pressure-sensitive adhesive is adjusted to fall within the range, the effects of the present invention can be more effectively expressed.

The metallocene-based olefin resin is also available as a commercial product. Examples of such commercial product include some products in the "Tafmer" (trademark) series (e.g., Tafmer PN-3560) manufactured by Mitsui Chemicals, Inc., and some products in the "Vistamaxx" (trademark) series (e.g., Vistamaxx 3000, Vistamaxx 6202, Vistamaxx 7010, and Vistamaxx 7050) manufactured by Exxon Mobil Corporation.

The hydrocarbon-based tackifiers may be used alone or in combination thereof.

Any appropriate hydrocarbon-based tackifier may be adopted as the hydrocarbon-based tackifier to the extent that the effects of the present invention are not impaired. Examples of such hydrocarbon-based tackifier include an aliphatic hydrocarbon-based tackifier, an alicyclic hydrocarbon-based tackifier, an aliphatic-alicyclic hydrocarbon-based tackifier, and a hydrogenated hydrocarbon-based tackifier. The hydrocarbon-based tackifier is more preferably a hydrocarbon-based tackifier free of an aromatic structure. The adoption of the hydrocarbon-based tackifier free of an aromatic structure can provide an olefin-based hot-melt pressure-sensitive adhesive more sufficiently suppressed in odor.

The content of the hydrocarbon-based tackifier in the olefin-based hot-melt pressure-sensitive adhesive is preferably from 75 wt % to 15 wt %, more preferably from 70 wt % to 20 wt %, still more preferably from 65 wt % to 25 wt %, particularly preferably from 60 wt % to 30 wt % When the content of the hydrocarbon-based tackifier in the hot-melt pressure-sensitive adhesive is adjusted to fall within the range, the pressure-sensitive adhesive property of the olefin-based hot-melt pressure-sensitive adhesive can be sufficiently expressed.

The oil components may be used alone or in combination thereof.

Any appropriate oil component may be adopted as the oil component to the extent that the effects of the present invention are not impaired. When the olefin-based hot-melt pressure-sensitive adhesive contains the oil component, the viscosity of the olefin-based hot-melt pressure-sensitive adhesive can be appropriately adjusted, and the pressure-sensitive adhesive property of the olefin-based hot-melt pressure-sensitive adhesive can be appropriately adjusted. Such oil component is preferably a paraffin oil, such as liquid paraffin. When the olefin-based hot-melt pressure-sensitive adhesive contains the paraffin oil, an olefin-based hot-melt pressure-sensitive adhesive more sufficiently suppressed in odor can be provided.

The content of the oil component in the olefin-based hot-melt pressure-sensitive adhesive is preferably from 40 wt % to 5 wt %, more preferably from 35 wt % to 6 wt %, still more preferably from 30 wt % to 8 wt %, particularly preferably from 25 wt % to 10 wt %. When the content of the oil component in the olefin-based hot-melt pressure-sensitive adhesive is adjusted to fall within the range, the viscosity of the olefin-based hot-melt pressure-sensitive adhesive can be more appropriately adjusted, and the pressure-sensitive adhesive property of the olefin-based hot-melt pressure-sensitive adhesive can be appropriately adjusted. In addition, when the content of the oil component in the olefin-based hot-melt pressure-sensitive adhesive is adjusted to fall within the range, an olefin-based hot-melt pressure-sensitive adhesive even more sufficiently suppressed in odor can be provided.

The olefin-based hot-melt pressure-sensitive adhesive may contain any appropriate other component to the extent that the effects of the present invention are not impaired. Examples of such other component include liquid paraffin, an antioxidant, a UV absorber, a light stabilizer, and a fluorescence agent. Such other components may be used alone or in combination thereof.

In the pressure-sensitive adhesive layer, an additive, such as a tackifier, a softener, a polyolefin-based resin, a silicone-based polymer, a liquid acrylic copolymer, a phosphoric acid ester-based compound, an age inhibitor, a light stabilizer, a UV absorber, a surface lubricant, a leveling agent, a plasticizer, a low-molecular weight polymer, an antioxidant, a corrosion inhibitor, a polymerization inhibitor, a silane coupling agent, an inorganic or organic filler (e.g., calcium oxide, magnesium oxide, silica, zinc oxide, or titanium oxide), metal powder, a colorant, a pigment, a heat stabilizer, may be appropriately added as required for the purpose of, for example, pressure-sensitive adhesive characteristic control.

The pressure-sensitive adhesive layer preferably contains a tackifier for the purpose of, for example, pressure-sensitive adhesive characteristic control.

Examples of the tackifier include a hydrocarbon-based tackifier, a terpene-based tackifier, a rosin-based tackifier, a phenol-based tackifier, an epoxy-based tackifier, a polyamide-based tackifier, an elastomer-based tackifier, and a ketone-based tackifier. The tackifiers may be used alone or in combination thereof.

Examples of the hydrocarbon-based tackifier include an aliphatic hydrocarbon resin, an aromatic hydrocarbon resin (e.g., a xylene resin), an aliphatic cyclic hydrocarbon resin, an aliphatic-aromatic petroleum resin (e.g., a styrene-olefin-based copolymer), an aliphatic-alicyclic petroleum resin, a hydrogenated hydrocarbon resin, a coumarone-based resin, and a coumarone-indene-based resin.

Examples of the terpene-based tackifier include: terpene-based resins, such as an α-pinene polymer and a β-pinene polymer; and modified terpene-based resins obtained by modification (e.g., phenol modification, aromatic modification, or hydrogenation modification) of the terpene-based resins (e.g., a terpene-phenol-based resin, a styrene-modified terpene-based resin, and a hydrogenated terpene-based resin).

Examples of the rosin-based tackifier include: unmodified rosins (raw rosins), such as gum rosin and wood rosin; modified rosins (e.g., hydrogenated rosin, disproportionated rosin, polymerized rosin, and other chemically modified rosins) obtained by modifying those unmodified rosins by hydrogenation, disproportionation, polymerization, and the like; and various other rosin derivatives.

Examples of the phenol-based tackifier include resol-type or novolac-type alkyl phenols.

The tackifier may be a tackifier commercially available as a blend with an olefin resin or a thermoplastic elastomer.

The surface of the pressure-sensitive adhesive layer may be subjected to a surface treatment intended for pressure-sensitive adhesive property control, bonding workability, or the like, such as a corona discharge treatment, a UV irradiation treatment, a flame treatment, a plasma treatment, or a sputter etching treatment, as required.

<Release Layer>

As described in FIG. 1, for example, any appropriate release layer may be arranged on each of a surface b (100b) side of the base material layer B (100) in the portion P1 (1001), a surface c (100c) side of the base material layer B (100) in the portion P2 (1002), a surface d (100d) side of the base material layer B (100) in the portion P2 (1002), and a surface e (100e) side of the base material layer B (100) in the portion P3 (1003) so that the tape may be folded into the Z shape before its use, and a state in which the tape is folded into the Z shape may be developed at the time of the use.

The thickness of the release layer fixing tape is preferably from 0.1 µm to 7.0 µm, more preferably from 0.2 mm to 6.0 µm, still more preferably from 0.3 µm to 5.0 µm, particularly preferably from 0.4 µm to 4.0 µm, most preferably from 0.5 µm to 3.0 µm. When the thickness of the release layer falls within the range, a state in which the ultrasmall fixing tape of the present invention is folded into a Z shape is easily maintained, and the state in which the tape is folded into the Z shape is easily developed at the time of its use. In addition, even in the case where the length of the tape in the longitudinal direction or widthwise direction is short, the tape can be more easily extended without rupturing, and can be more sufficiently ultrasmall-sized. In addition, the tape can express such a strength as to be harder to rupture even when sufficiently extended, and the tape can express more sufficient elastic recoverability and hence can exhibit a more satisfactory fitting feeling even after its sufficient extension.

The release layer may be only one layer, or may be a laminate of two or more layers.

Any appropriate release layer may be adopted as the release layer to the extent that the effects of the present invention are not impaired. A preferred example of such release layer is a release layer formed of any appropriate peeling agent.

Examples of the peeling agent include: silicone-based peeling agents, such as a condensation-type or addition-type thermosetting silicone-based peeling agent and a radiation-curable-type silicone-based peeling agent capable of being cured by UV light or an electron beam; fluorine-based peeling agents each containing an acrylic copolymer obtained by polymerization of a fluorine-containing ester of (meth)acrylic acid and an alkyl ester of (meth)acrylic acid having an alkyl group having 8 or less carbon atoms or the like; and long-chain alkyl-based peeling agents each containing an acrylic copolymer obtained by polymerization of an alkyl ester of (meth)acrylic acid having a long-chain alkyl group having 12 to 22 carbon atoms and an alkyl ester of (meth)acrylic acid having an alkyl group having 8 or less carbon atoms (see, for example, JP 29-3144 B2 and JP 29-7333 B2). The peeling agent is preferably a silicone-based peeling agent because the effects of the present invention can be expressed to a larger extent.

<Engaging Portion>

In the ultrasmall fixing tape of the present invention, an engaging portion may be included in at least part of the extending portion.

Any appropriate engaging portion may be adopted as such engaging portion to the extent that the effects of the present invention are not impaired as long as the portion has such a function as to be capable of engaging with any other site. Such engaging portion is preferably a pressure-sensitive adhesive layer or a hook material. The engaging portion may be a portion in which the pressure-sensitive adhesive layer and the hook material coexist.

At least part of the engaging portion may be colored. When at least part of the engaging portion is colored, a user can easily find the engaging portion, and hence can easily understand, for example, a place to be picked when the tape is picked with a hand and extended.

The shear adhesive strength of the engaging portion at a temperature of 23° C. and a humidity of 50% is preferably 6 N/1.95 mm$^2$ or more, more preferably from 6 N/1.95 mm$^2$ to 25 N/1.95 mm$^2$, Still more preferably from 6 N/1.95 mm$^2$ to 22 N/1.95 mm$^2$, particularly preferably from 6 N/1.95 mm$^2$ to 20 N/1.95 mm$^2$, most preferably from 6 N/1.95 mm$^2$ to 18 N/1.95 mm$^2$. When the shear adhesive strength of the engaging portion falls within the range, at the time of, for example, such securing with the ultrasmall fixing tape of the present invention that a used absorbent article folded into a small size does not open, even an ultrasmall-sized fixing tape like the ultrasmall fixing tape of the present invention can be reliably secured without the loosening of the secured site, and hence the used absorbent article folded into a small size can be suppressed from returning to its original shape.

When the engaging portion is a pressure-sensitive adhesive layer, a mode in which the pressure-sensitive adhesive layer is arranged in at least part of the extending portion is typically given. More specifically, for example, a pressure-sensitive adhesive layer formed as follows is given: a material for the pressure-sensitive adhesive layer is applied to the one surface e ranging from the site of the folding-processed portion V2 to the other end portion E2 in the longitudinal direction of the base material layer B, and is subjected to, for example, UV curing to form the layer.

Figure 3:
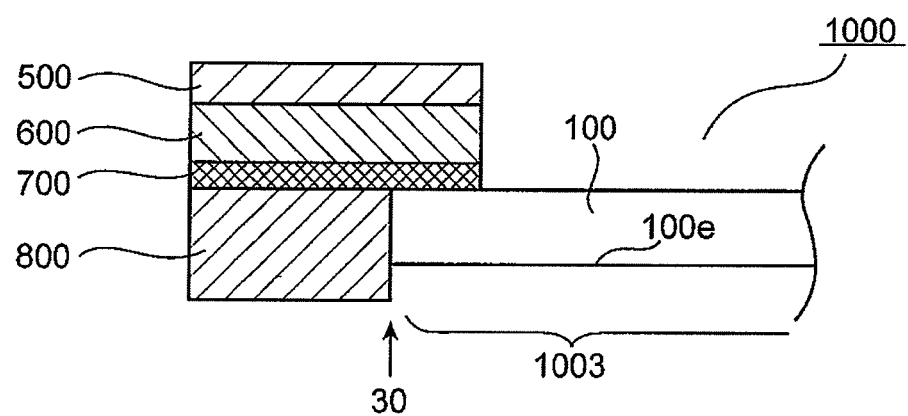
FIG. 3 is a schematic sectional view of a mode in which an extending portion includes an engaging portion in at least part thereof.

When the engaging portion is a hook material, a mode in which the hook material is arranged in at least part of the extending portion is given. FIG. 3 is a schematic sectional view of the mode in which the hook material is included as the engaging portion in at least part of the extending portion. In FIG. 3, a hook material (800) is arranged in the end portion E2 (30) of the portion P3 (1003) of the ultrasmall fixing tape (1000) of the present invention by a laminate of a non-woven fabric layer (500), a plastic film (600), and a pressure-sensitive adhesive layer (700).

Any appropriate non-woven fabric may be adopted as the non-woven fabric layer (500) to the extent that the effects of the present invention are not impaired. Examples of such non-woven fabric include a spunbonded non-woven fabric, a thermally bonded non-woven fabric, a bonded and joined non-woven fabric, an air-through non-woven fabric, a meltblown non-woven fabric, a spunbonded meltblown spunbonded non-woven fabric, a spunbonded meltblown meltblown spunbonded non-woven fabric, an unjoined non-woven fabric, an electrospun non-woven fabric, a flashspun non-woven fabric (e.g., TYVEK™ from DuPont), and a carded non-woven fabric. Of the above-mentioned non-woven fabrics, a spunbonded non-woven fabric, a thermally bonded non-woven fabric, a bonded and joined non-woven fabric, an air-through non-woven fabric, a meltblown non-woven fabric, a spunbonded meltblown spunbonded non-woven fabric, and a spunbonded meltblown meltblown spunbonded non-woven fabric are preferred, a spunbonded non-woven fabric and an air-through non-woven fabric are more preferred, and a spunbonded non-woven fabric is still more preferred.

The non-woven fabric may contain fiber that is a homogeneous structural body, or may contain conjugate fiber that is a bicomponent structural body, such as a core-sheath structure, a side-by-side structure, a sea-island structure, or any other bicomponent structure. Detailed description of the non-woven fabric may be found in, for example, "Nonwoven Fabric Primer and Reference Sampler", E. A. Vaughn, Association of the Nonwoven Fabrics Industry, third edition (1992).

Any appropriate fiber may be adopted as the fiber forming the non-woven fabric to the extent that the effects of the present invention are not impaired. Such fiber contains, for example, polyolefin (such as polypropylene or polyethylene), polyester, polyamide, polyurethane, an elastomer, rayon, cellulose, acrylic, a copolymer thereof, or a blend thereof, or a mixture thereof. Such fiber preferably includes at least one kind selected from fiber of polyolefin (polyolefin fiber), fiber of polyester (polyester fiber), and conjugate fiber of two or more kinds of resins selected from polyolefin and polyester because the effects of the present invention can be more effectively expressed.

Examples of the polyolefin fiber include polypropylene fiber, polyethylene fiber, and α-olefin copolymer fiber. The polyolefin fiber is preferably polypropylene fiber or polyethylene fiber, more preferably polypropylene fiber because the effects of the present invention can be more effectively expressed.

Examples of the polyester fiber include polyethylene terephthalate (PET) fiber, polylactic acid fiber, and polyglycolic acid fiber. The polyester fiber is preferably polyethylene terephthalate (PET) fiber because the effects of the present invention can be more effectively expressed.

Examples of the conjugate fiber of two or more kinds of resins selected from the polyolefin and the polyester include fiber having a core-sheath structure, fiber having a side-by-side structure, and hollow fiber. The term "conjugate fiber of two or more kinds of resins selected from the polyolefin and the polyester" as used herein means conjugate fiber of two or more kinds of polyolefin resins, conjugate fiber of two or more kinds of polyester resins, and conjugate fiber of one or more kinds of polyolefin resins and one or more kinds of polyester resins.

Specific examples of the conjugate fiber of two or more kinds of resins selected from the polyolefin and the polyester include: fiber having a core-sheath structure, the fiber having one of two kinds of polyolefin in its core portion and the other thereof in its sheath portion; fiber having a core-sheath structure, the fiber having the polyester in its core portion and the polyolefin in its sheath portion; and fiber in the polyolefin and the polyester form a side-by-side structure.

The fiber forming the non-woven fabric may be crimpable fiber. An example of the crimpable fiber is fiber having a side-by-side structure or an unevenly distributed core-sheath structure, and containing two components having different coagulation points, the fiber expressing fine coil-like crimps each having a relatively small radius as a result of the preceding solidification and shrinkage of a component having the higher solidifying point at the time of the phase change of the fiber from a molten state to a solid state.

The fiber forming the non-woven fabric may contain any appropriate other component to the extent that the effects of the present invention are not impaired. Examples of such other component include any other polymer, a tackifier, a plasticizer, an antidegradant, a pigment, a dye, an antioxidant, an antistatic agent, a lubricant, a foaming agent, a heat stabilizer, a light stabilizer, an inorganic filler, and an organic filler. Those components may be used alone or in combination thereof. The content of the other component in the fiber forming the non-woven fabric is preferably 10 wt % or less, more preferably 7 wt % or less, still more preferably 5 wt % or less, particularly preferably 2 wt % or less, most preferably 1 wt % or less.

Any appropriate plastic film may be adopted as the plastic film (600) to the extent that the effects of the present invention are not impaired. Examples of such plastic film include polyolefin films, such as a polyethylene film (e.g., a linear low-density polyethylene film, a low-density polyethylene film, a medium-density polyethylene film, or a high-density polyethylene film) and a polypropylene film (e.g., a random polypropylene film or a block polypropylene film).

The foregoing description of the pressure-sensitive adhesive layer is incorporated as the description of the pressure-sensitive adhesive layer (700).

<<Production of Ultrasmall Fixing Tape>>

The ultrasmall fixing tape of the present invention may be produced by any appropriate method. Such method is, for example, as described below. The base material layer B is prepared, and a material for securing means is applied to the one surface a ranging from the one end portion E1 to the site of the folding-processed portion V1 in the longitudinal direction of the base material layer B, and is subjected to, for example, UV curing to form the securing means. A material for a release layer is applied to the other surface b ranging from the one end portion E1 to the site of the folding-processed portion V1 in the longitudinal direction of the base material layer B, and is subjected to, for example, UV curing to form the release layer. Thus, the portion P1 having a laminated structure "securing means/base material layer B/release layer" is formed. Meanwhile, a material for a pressure-sensitive adhesive layer is applied to the one surface c ranging from the site of the folding-processed portion V1 to the site of the folding-processed portion V2 in the longitudinal direction of the base material layer B, and is subjected to, for example, UV curing to form the pressure-sensitive adhesive layer. A material for a release layer is applied to the other surface d ranging from the site of the folding-processed portion V1 to the site of the folding-processed portion V2 in the longitudinal direction of the base material layer B, and is subjected to, for example, UV curing to form the release layer. Thus, the portion P2 having a laminated structure "pressure-sensitive adhesive layer/base material layer B/release layer" is formed. Further, meanwhile, a material for a pressure-sensitive adhesive layer is applied to the one surface e ranging from the site of the folding-processed portion V2 to the other end portion E2 in the longitudinal direction of the base material layer B, and is subjected to, for example, UV curing to form the pressure-sensitive adhesive layer. Thus, the portion P3 having a laminated structure "pressure-sensitive adhesive layer/base material layer B" is formed, and hence the ultrasmall fixing tape of the present invention can be obtained. In addition, in the method, the order in which the respective layers are formed may be different from that described above, and the formation of each of the folding-processed portion V1 and the folding-processed portion V2 may be performed at any timing. Any appropriate means may be adopted as means for forming each of the folding-processed portion V1 and the folding-processed portion V2. Further, such engaging portion as described in the foregoing may be arranged.

<<Applications of Ultrasmall Fixing Tape>>

The ultrasmall fixing tape of the present invention can be used in any appropriate absorbent article in which the effects of the present invention can be effectively utilized. That is, an absorbent article of the present invention includes the ultrasmall fixing tape of the present invention. Such absorbent article is typically, for example, a sanitary article. Examples of such sanitary article include a disposable diaper, a sanitary napkin, an incontinence pad, a supporter, and a mask.

<<Disposal Method Involving Using Ultrasmall Fixing Tape>>

The ultrasmall fixing tape of the present invention can be used as a disposal tape for various wastes. Typical examples of such wastes include any appropriate absorbent articles, and specific examples thereof include sanitary articles, such as a disposable diaper, a sanitary napkin, an incontinence pad, a supporter, and a mask.

A disposal method involving using the ultrasmall fixing tape of the present invention involves, for example, pulling the extending portion of the ultrasmall fixing tape of the present invention secured to a portion of an absorbent article to be disposed of to develop a state in which the tape is folded into a Z shape, and further pulling the extending portion to secure the tape to another portion of the absorbent article in such a form that the tape mediates between the portions to prevent the absorbent article folded into a small size from opening.

Figure 4:
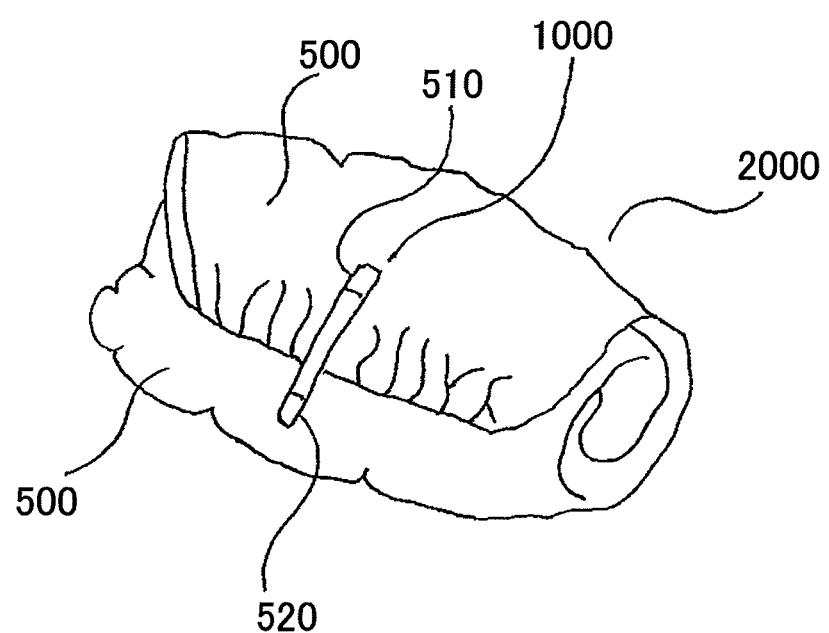
FIG. 4 is a perspective view for illustrating one embodiment of a disposal method involving using an ultrasmall fixing tape of the present invention.

FIG. 4 is a perspective view for illustrating one embodiment of the disposal method involving using the ultrasmall fixing tape of the present invention. In FIG. 4, the ultrasmall fixing tape (1000) of the present invention is secured to the site of a portion Y (510) of a member X (500) of a disposable diaper (2000) by its securing means, and its extending portion is pulled to develop a state in which the tape is folded into a Z shape. The extending portion is further pulled to secure the tape to the site of a portion Z (520) of the member X (500) of the absorbent article in such a form that the tape mediates between the portions to prevent the diaper (2000) folded into a small size from opening.

EXAMPLES

The present invention is hereinafter specifically described by way of Examples. However, the present invention is by no means limited to these Examples. Test and evaluation methods in Examples and the like are as described below. In addition, "part(s)" means "part(s) by weight" and "%" means "wt %" unless otherwise stated.

<Upper Yield Strength and Extension at Rupture>

Each of Z-shaped tapes of Examples and Comparative Examples was cut into a width of 25 mm, and was then developed. The tape was set in a tension testing machine (manufactured by Shimadzu Corporation: AG-20 kNG) at a distance between chucks of 50 mm in its lengthwise direction, and was extended at a tension speed of 300 mm/min to its rupture point.

An upper yield strength and an extension at rupture were identified from the measurement of S-S data. When the tape has no upper yield point during its extension from 0% to 100%, an extension stress at the time of a strain of 100% is highest, and when the tape has an upper yield point, an extension stress at the time of a strain of less than 100% is highest, and the point is the upper yield point. In addition, its maximum extension amount is obtained as the extension at rupture (%).

<Permanent Strain Amount>

Each of the Z-shaped tapes of Examples and Comparative Examples was cut into a width of 25 mm, and was then developed. The tape was set in a tension testing machine (manufactured by Shimadzu Corporation: AG-20 kNG) at a distance between chucks of 50 mm in its lengthwise direction, and was extended at a tension speed of 300 mm/min to 400%, followed by the returning of the extended tape at a tension speed of 1,000 mm/min to 0% (first stretching). The tape was removed from the chucks once, and the stretched tape was stretched at a distance between the chucks of 50 mm and at 300 mm/min by 100% again (second stretching). The tape was returned to 0% again, and this time, was stretched to 100% again without being removed from the chucks (third stretching). A permanent strain amount observed at the time of the third stretching (strain amount % at which no stress occurred) was defined as the permanent strain amount of the tape.

<Adhesive Strength to Hydrophobic PP Non-Woven Fabric>

Each of the Z-shaped tapes of Examples and Comparative Examples was cut into a width of 15 mm, and was then developed to prepare a sample having an adhesion area measuring 15 mm wide by 13 mm long. Meanwhile, a spunbonded non-woven fabric for a diaper back sheet (19 g/m$^2$) (hydrophobic type), 100% of the non-woven fabric being made of polypropylene, was bonded to a PP plate with an acrylic double-sided tape (manufactured by Nitto Denko Corporation: No. 5000NS). The sample was crimped onto the surface of the non-woven fabric in the designated adhesion area by reciprocating a load of 1 kg twice. After the crimping, the resultant was left at rest for 1 minute at room temperature (23° C.), and an adhesive strength was measured at an angle of 90° and a peel rate of 300 mm/min.

Example 1

HDPE (manufactured by Tosoh Corporation, product name: Nipolon Hard 1000) was loaded into the A layer of an extruder, and a product obtained by blending 95 parts of amorphous polyolefin (manufactured by Exxon Mobil Corporation, product name: Vistamaxx 7010) and 5 parts of a white pigment (titanium oxide, manufactured by DuPont, product name: Ti-Pure R103) was loaded into the B layer of the extruder, followed by the extrusion of an elastic film having a total thickness of 50 μm in which the thicknesses of the A layer, the B layer, and the A layer were 5 μm, 40 μm, and 5 μm, respectively.

A SIS-based pressure-sensitive adhesive (100 parts of a styrene-based thermoplastic elastomer (SIS, manufactured by Zeon Corporation, product name: Quintac 3520), 150 parts of a hydrogenated aromatic modified terpene resin (manufactured by Yasuhara Chemical Co., Ltd., product name: CLEARON M-105), and 80 parts of an aromatic modified terpene polymer (manufactured by Yasuhara Chemical Co., Ltd., product name: YS RESIN TO-L) was applied to each of the surface a (100a), surface c (100c), and surface e (100e) illustrated in FIG. 1 of the resultant elastic film so that its thickness after curing became 70 μm. A product obtained by blending 100 parts of a UV-curable silicone-based peeling agent (manufactured by Momentive Performance Materials Inc., product name: UV9300) and 3 parts of a UV-curable silicone-based peeling agent (manufactured by Momentive Performance Materials Inc., product name: UV9380C) was applied to each of the surface b (100b) and surface d (100d) illustrated in FIG. 1 of the film so that the thickness of a release layer after curing became 0.7 μm.

Each of the applied layers was cured by UV irradiation (irradiation conditions: manufactured by Fusion UV Systems Japan, CV-1100-G, irradiation amount: 1,200 W/cm$^2$, line speed: 50 m/min).

The resultant laminated film was cut so as to have a length in its longitudinal direction of 60 mm and a length in its widthwise direction of 15 mm, and was folded into a Z shape so that its release layers were positioned inside. Thus, a fixing tape (1) having a length in its longitudinal direction of 20 mm and a length in its widthwise direction of 15 mm was obtained.

The results are shown in Table 1.

Example 2

A laminated film was obtained in the same manner as in Example 1 except that HDPE (manufactured by Tosoh Corporation, product name: Nipolon Hard 1000) was loaded into the A layer of an extruder, and a product obtained by blending 95 parts of amorphous polyolefin (manufactured by Exxon Mobil Corporation, product name: Vistamaxx 7010) and 5 parts of a white pigment (titanium oxide, manufactured by DuPont, product name: Ti-Pure R103) was loaded into the B layer of the extruder, followed by the extrusion of an elastic film having a total thickness of 75 μm in which the thicknesses of the A layer, the B layer, and the A layer were 7.5 μm, 60 μm, and 7.5 μm, respectively. The resultant laminated film was cut so as to have a length in its longitudinal direction of 60 mm and a length in its widthwise direction of 15 mm, and was folded into a Z shape so that its release layers were positioned inside. Thus, a fixing tape (2) having a length in its longitudinal direction of 20 mm and a length in its widthwise direction of 15 mm was obtained.

The results are shown in Table 1.

Example 3

A laminated film was obtained in the same manner as in Example 1 except that HDPE (manufactured by Tosoh Corporation, product name: Nipolon Hard 1000) was loaded into the A layer of an extruder, and a product obtained by blending 95 parts of amorphous polyolefin (manufactured by Exxon Mobil Corporation, product name: Vistamaxx 7010) and 5 parts of a white pigment (titanium oxide, manufactured by DuPont, product name: Ti-Pure R103) was loaded into the B layer of the extruder, followed by the extrusion of an elastic film having a total thickness of 100 μm in which the thicknesses of the A layer, the B layer, and the A layer were 10 μm, 80 μm, and 10 μm, respectively. The resultant laminated film was cut so as to have a length in its longitudinal direction of 60 mm and a length in its widthwise direction of 15 mm, and was folded into a Z shape so that its release layers were positioned inside. Thus, a fixing tape (3) having a length in its longitudinal direction of 20 mm and a length in its widthwise direction of 15 mm was obtained.

The results are shown in Table 1.

Example 4

Random PP (manufactured by Japan Polypropylene Corporation: NOVATEC-PP EG8) was extruded from a T-die extrusion molding machine set to 220° C. to be laminated onto a spunbonded non-woven fabric using a hydrophobic PP resin (36 gsm) so as to have a basis weight of 32 gsm. A SIS-based pressure-sensitive adhesive (100 parts of a styrene-based thermoplastic elastomer (SIS, manufactured by Zeon Corporation, product name: Quintac 3520), 150 parts of a hydrogenated aromatic modified terpene resin (manufactured by Yasuhara Chemical Co., Ltd., product name: CLEARON M-105), and 80 parts of an aromatic modified terpene polymer (manufactured by Yasuhara Chemical Co., Ltd., product name: YS RESIN TO-L) was applied to the random PP resin layer surface of the resultant laminated film so that its thickness after curing became 40 μm. A hook material having a width of 13 mm (manufactured by Binder, 85445) was laminated onto the applied layer. Thus, an engaging portion A was obtained.

The resultant engaging portion A was bonded to the surface of the fixing tape (1) obtained in Example 1 opposite to the surface e (100e) in the portion P3 (1003) illustrated in FIG. 1 in such a mode as illustrated in FIG. 3 so that the amount in which the portion lapped over the applied layer of the SIS-based pressure-sensitive adhesive became 10 mm. Thus, a fixing tape (4) with a hook was obtained.

An engaging product in the fixing tape (4) had a length in its longitudinal direction including the lapping amount of 10 mm (i.e., the length of the spunbonded non-woven fabric using the hydrophobic PP resin) of 15 mm, a length of the hook material portion of 15 mm, and a length in its widthwise direction of 13 mm.

The results are shown in Table 1.

Example 5

A fixing tape (5) with a hook was obtained in the same manner as in Example 4 except that the fixing tape (2) obtained in Example 2 was used instead of the fixing tape (1) obtained in Example 1.

The results are shown in Table 1.

Example 6

A fixing tape (6) with a hook was obtained in the same manner as in Example 4 except that the fixing tape (3) obtained in Example 3 was used instead of the fixing tape (1) obtained in Example 1.

The results are shown in Table 1.

Comparative Example 1

LDPE (manufactured by Tosoh Corporation, product name: Petrocene 251R) was loaded into the A layer of an extruder, and a product obtained by blending 95 parts of LDPE (manufactured by Tosoh Corporation, product name: Petrocene 251R) and 5 parts of a white pigment (titanium oxide, manufactured by DuPont, product name: Ti-Pure R103) was loaded into the B layer of the extruder, followed by the extrusion of an elastic film having a total thickness of 50 μm in which the thicknesses of the A layer, the B layer, and the A layer were 5 μm, 40 μm, and 5 μm, respectively.

A SIS-based pressure-sensitive adhesive (100 parts of a styrene-based thermoplastic elastomer (SIS, manufactured by Zeon Corporation, product name: Quintac 3520), 150 parts of a hydrogenated aromatic modified terpene resin (manufactured by Yasuhara Chemical Co., Ltd., product name: CLEARON M-105), and 80 parts of an aromatic modified terpene polymer (manufactured by Yasuhara Chemical Co., Ltd., product name: YS RESIN TO-L) was applied to each of the surface a (100a), surface c (100c), and surface e (100e) illustrated in FIG. 1 of the resultant elastic film so that its thickness after curing became 70 μm. A product obtained by blending 100 parts of a UV-curable silicone-based peeling agent (manufactured by Momentive Performance Materials Inc., product name: UV9300) and 3 parts of a UV-curable silicone-based peeling agent (manufactured by Momentive Performance Materials Inc., product name: UV9380C) was applied to each of the surface b (100b) and surface d (100d) illustrated in FIG. 1 of the film so that the thickness of a release layer after curing became 15 μm.

Each of the applied layers was cured by UV irradiation (irradiation conditions: manufactured by Fusion UV Systems Japan, CV-1100-G, irradiation amount: 1,200 W/cm$^2$, line speed: 50 m/min).

The resultant laminated film was cut so as to have a length in its longitudinal direction of 60 mm and a length in its widthwise direction of 15 mm, and was folded into a Z shape so that its release layers were positioned inside. Thus, a fixing tape (C1) having a length in its longitudinal direction of 20 mm and a length in its widthwise direction of 15 mm was obtained.

The results are shown in Table 1.

Comparative Example 2

LDPE (manufactured by Tosoh Corporation, product name: Petrocene 251R) was loaded into the A layer of an extruder, and a product obtained by blending 95 parts of LDPE (manufactured by Tosoh Corporation, product name: Petrocene 251R) and 5 parts of a white pigment (titanium oxide, manufactured by DuPont, product name: Ti-Pure R103) was loaded into the B layer of the extruder, followed by the extrusion of an elastic film having a total thickness of 80 μm in which the thicknesses of the A layer, the B layer, and the A layer were 8 μm, 64 μm, and 8 μm, respectively. A fixing tape (C2) was obtained in the same manner as in Comparative Example 1 except that this elastic film was used as the elastic film.

The results are shown in Table 1.

Comparative Example 3

LDPE (manufactured by Tosoh Corporation, product name: Petrocene 251R) was loaded into the A layer of an extruder, and a product obtained by blending 95 parts of LDPE (manufactured by Tosoh Corporation, product name: Petrocene 251R) and 5 parts of a white pigment (titanium oxide, manufactured by DuPont, product name: Ti-Pure R103) was loaded into the B layer of the extruder, followed by the extrusion of an elastic film having a total thickness of 100 μm in which the thicknesses of the A layer, the B layer, and the A layer were 10 μm, 80 μm, and 10 μm, respectively. A fixing tape (C3) was obtained in the same manner as in Comparative Example 1 except that this elastic film was used as the elastic film.

The results are shown in Table 1.

TABLE 1

| | | Example | | | | | |
|---|---|---|---|---|---|---|---|
| | | 1 | 2 | 3 | 4 | 5 | 6 |
| A layer resin (1) | | Nipolon-Hard 1000 | ← | ← | ← | ← | ← |
| B layer resin (1) | | Vistamaxx 7010 | ← | ← | ← | ← | ← |
| B layer resin (2) | | TiO$^2$ | ← | ← | ← | ← | ← |
| B layer formulation (1)/(2) | | 95/5 | ← | ← | ← | ← | ← |
| A/B/A thickness | μm | 5/40/5 | 7.5/60/7.5 | 10/80/10 | 7.5/60/7.5 | 8/64/8 | 10/80/10 |
| Total thickness of film | μm | 50 | 75 | 100 | 75 | 80 | 100 |
| Adhesion mechanism for disposal | | Hot-melt pressure-sensitive adhesive | Hot-melt pressure-sensitive adhesive | Hot-melt pressure-sensitive adhesive | Hook material | Hook material | Hook material |
| S-S upper yield strength | N/25 mm | 6.4 | 8.2 | 12.7 | 6.3 | 8.1 | 12.8 |
| Extension at rupture | % | 820 | 1,130 | 910 | 834 | 980 | 890 |
| Permanent strain amount | % | 13.4 | 15.8 | 13.1 | 13.8 | 14.8 | 13.6 |
| Adhesive strength to hydrophobic PP non-woven fabric | N (adhesion area measuring 13 mm by 15 mm) | 11.8 | 12.1 | 13.2 | 13.5 | 13.1 | 13.3 |

TABLE 1-continued

|  |  | Comparative Example | | |
|---|---|---|---|---|
|  |  | 1 | 2 | 3 |
| A layer resin (1) |  | Petrocene 251R | ← | ← |
| B layer resin (1) |  | Petrocene 251R | ← | ← |
| B layer resin (2) |  | TiO$^2$ | ← | ← |
| B layer formulation (1)/(2) |  | 95/5 | ← | ← |
| A/B/A thickness | μm | 5/40/5 | 8/64/8 | 10/80/10 |
| Total thickness of film | μm | 50 | 80 | 100 |
| Adhesion mechanism for disposal |  | Hot-melt pressure-sensitive adhesive | Hot-melt pressure-sensitive adhesive | Hot-melt pressure-sensitive adhesive |
| S-S upper yield strength | N/25 mm | 20.3 | 21.9 | 26.3 |
| Extension at rupture | % | 621 | 652 | 685 |
| Permanent strain amount | % | 65 | 78 | 79 |
| Adhesive strength to hydrophobic PP non-woven fabric | N (adhesion area measuring 13 mm by 15 mm) | 12.1 | 11.9 | 12.1 |

INDUSTRIAL APPLICABILITY

The ultrasmall fixing tape of the present invention can be used in any appropriate absorbent article in which the effects of the present invention can be effectively utilized. That is, an absorbent article of the present invention includes the ultrasmall fixing tape of the present invention. Such absorbent article is typically, for example, a sanitary article. Examples of such sanitary article include a disposable diaper, a sanitary napkin, an incontinence pad, a supporter, and a mask.

REFERENCE SIGNS LIST 1000 ultrasmall fixing tape
1001 portion P1
1002 portion P2
1003 portion P3
100 base material layer B
100a surface a
100b surface b
100c surface c
100d surface d
100e surface e
200 securing means
300 pressure-sensitive adhesive tape
400 release layer
500 non-woven fabric layer
600 plastic film
700 pressure-sensitive adhesive layer
800 hook material
10 end portion E1
20a folding-processed portion V1
20b folding-processed portion V2
30 end portion E2
40 elastomer layer
50a olefin-based resin layer
50b olefin-based resin layer
2000 disposable diaper
500 member X
510 portion Y
520 portion Z

The invention claimed is:

1. A fixing tape, comprising:
a base material layer, that includes:
an extending portion; and
a non-extending portion connected to an end of the extending portion and that is substantially free from extending, wherein
the non-extending portion includes an adhesive in at least part thereof,
the base material layer comprises a stretchable laminate including an elastomer layer and an olefin-based resin layer arranged on at least one side of the elastomer layer,
the base material layer has a thickness that is from 50 μm to 125 μm,
the base material layer has an upper yield strength in a longitudinal direction thereof at a temperature of 23° C. and a humidity of 50% of from 5 N/25 mm to 15 N/25 mm, and
the base material layer has a permanent strain amount of 30% or less when the base material layer is extended in the longitudinal direction at an extension percentage of 400% and then returned to a steady state, subsequently extended in the longitudinal direction at an extension percentage of 100% and then returned to the steady state, and further extended in the longitudinal direction at an extension percentage of 100% at a temperature of 23° C. and a humidity of 50%.

2. The fixing tape according to claim 1, wherein the upper yield strength is from 5 N/25 mm to 10 N/25 mm.

3. The fixing tape according to claim 1, wherein the base material layer has an extension at rupture in the longitudinal direction at a temperature of 23° C. and a humidity of 50% of 600% or more.

4. The fixing tape according to claim 3, wherein the extension at rupture is from 600% to 1,500%.

5. The fixing tape according to claim 1, wherein the permanent strain amount is from 5% to 30%.

6. The fixing tape according to claim 1, wherein the extending portion includes an engaging portion in at least part thereof.

7. The fixing tape according to claim 6, wherein the engaging portion has a shear adhesive strength at a temperature of 23° C. and a humidity of 50% of 6 N/1.95 mm$^2$ or more.

8. The fixing tape according to claim 7, wherein the shear adhesive strength is from 6 N/1.95 mm$^2$ to 25 N/1.95 mm$^2$.

9. The fixing tape according to claim 6, wherein the engaging portion comprises a pressure-sensitive adhesive layer or a hook material.

10. The fixing tape according to claim 1, wherein the adhesive comprises a pressure-sensitive adhesive.

11. The fixing tape according to claim 10, wherein the pressure-sensitive adhesive comprises a hot-melt pressure-sensitive adhesive.

12. The fixing tape according to claim 1, wherein the fixing tape has a length in a longitudinal direction thereof of from 5 mm to 80 mm.

13. The fixing tape according to claim 12, wherein the length in the longitudinal direction is from 10 mm to 50 mm.

14. The fixing tape according to claim 1, wherein the fixing tape has a length in a widthwise direction thereof of from 5 mm to 40 mm.

15. The fixing tape according to claim 14, wherein the length in the widthwise direction is from 5 mm to 20 mm.

16. The fixing tape according to claim 1, wherein the olefin-based resin layer contains a non-elastomeric olefin-based resin.

17. The fixing tape according to claim 16, wherein the non-elastomeric olefin-based resin contains an α-olefin homopolymer.

18. The fixing tape according to claim 17, wherein the α-olefin homopolymer comprises at least one kind selected from polyethylene (PE) and homopolypropylene (PP).

19. The fixing tape according to claim 17, wherein the α-olefin homopolymer contains at least one kind selected from high-density polyethylene (HDPE) and homopolypropylene (PP).

20. The fixing tape according to claim 1, wherein the elastomer layer contains an olefin-based elastomer.

21. The fixing tape according to claim 20, wherein the olefin-based elastomer comprises an α-olefin-based elastomer.

22. The fixing tape according to claim 21, wherein the α-olefin-based elastomer comprises at least one kind selected from an ethylene-based elastomer and a propylene-based elastomer.

23. The fixing tape according to claim 21, wherein the α-olefin-based elastomer comprises a metallocene-based α-olefin elastomer.

24. The fixing tape according to claim 1, wherein the fixing tape has a folding-processed portion in at least one site.

25. An absorbent article, comprising:
the fixing tape of claim 1.

* * * * *